(12) United States Patent
Crainiceanu et al.

(10) Patent No.: US 9,888,876 B2
(45) Date of Patent: Feb. 13, 2018

(54) METHOD OF ANALYZING MULTI-SEQUENCE MRI DATA FOR ANALYSING BRAIN ABNORMALITIES IN A SUBJECT

(71) Applicants: THE JOHNS HOPKINS UNIVERSITY, Baltimore, MD (US); NATIONAL INSTITUTES OF HEALTH, Rockville, MD (US); THE HENRY M. JACKSON FOUNDATION FOR THE ADVANCEMENT OF MILITARY MEDICINE, INC., Bethesda, MD (US)

(72) Inventors: Ciprian Crainiceanu, Baltimore, MD (US); Arthur Jeffrey Goldsmith, New York, NY (US); Dzung Pham, Alexandria, VA (US); Daniel S. Reich, Washington, DC (US); Navid Shiee, North Bethesda, MD (US); Russell T. Shinohara, Philadelphia, PA (US); Elizabeth M. Sweeney, Baltimore, MD (US)

(73) Assignees: The Johns Hopkins University, Baltimore, MD (US); The Henry M. Jackson Foundation for the Advancement of Military Medicine, Inc., Bethesda, MD (US); The United States of America, as Represented by the Secretary, Department of Health and Human Services, Washington, DC (US)

( * ) Notice: Subject to any disclaimer, the term of this patent is extended or adjusted under 35 U.S.C. 154(b) by 541 days.

(21) Appl. No.: 14/385,509

(22) PCT Filed: Mar. 21, 2013

(86) PCT No.: PCT/US2013/033334
§ 371 (c)(1),
(2) Date: Sep. 16, 2014

(87) PCT Pub. No.: WO2013/142706
PCT Pub. Date: Sep. 26, 2013

(65) Prior Publication Data
US 2015/0045651 A1 Feb. 12, 2015

Related U.S. Application Data

(60) Provisional application No. 61/613,569, filed on Mar. 21, 2012.

(51) Int. Cl.
*A61B 5/00* (2006.01)
*A61B 5/055* (2006.01)
(Continued)

(52) U.S. Cl.
CPC ............ *A61B 5/4064* (2013.01); *A61B 5/055* (2013.01); *G01R 33/3614* (2013.01);
(Continued)

(58) Field of Classification Search
CPC combination set(s) only.
See application file for complete search history.

(56) References Cited

U.S. PATENT DOCUMENTS

2005/0267357 A1 12/2005 Rao et al.
2006/0104494 A1* 5/2006 Collins ............... G06F 19/3443
382/128
(Continued)

FOREIGN PATENT DOCUMENTS

WO 96-42070 A1 12/1996
WO 2010-115885 A1 10/2010

*Primary Examiner* — Tsung-Yin Tsai
(74) *Attorney, Agent, or Firm* — Johns Hopkins Technology Ventures

(57) ABSTRACT

The present invention, referred to as Oasis is Automated Statistical Inference for Segmentation (OASIS), is a fully automated and robust statistical method for cross-sectional MS lesion segmentation. Using intensity information from multiple modalities of MRI, a logistic regression model assigns voxel-level probabilities of lesion presence. The OASIS model produces interpretable results in the form of regression coefficients that can be applied to imaging studies quickly and easily. OASIS uses intensity-normalized brain MRI volumes, enabling the model to be robust to changes in scanner and acquisition sequence. OASIS also adjusts for intensity inhomogeneities that preprocessing bias field correction procedures do not remove, using BLUR volumes. This allows for more accurate segmentation of brain areas that are highly distorted by inhomogeneities, such as the
(Continued)

cerebellum. One of the most practical properties of OASIS is that the method is fully transparent, easy to implement, and simple to modify for new data sets.

19 Claims, 12 Drawing Sheets

(51) Int. Cl.
  *G06T 7/00* (2017.01)
  *G01R 33/36* (2006.01)
  *G01R 33/385* (2006.01)
  *G01R 33/56* (2006.01)
(52) U.S. Cl.
  CPC .......... *G01R 33/385* (2013.01); *G06T 7/0012* (2013.01); *G01R 33/5608* (2013.01); *G06T 2207/10088* (2013.01); *G06T 2207/20076* (2013.01); *G06T 2207/30016* (2013.01); *G06T 2207/30096* (2013.01)

(56) References Cited

U.S. PATENT DOCUMENTS

| | | | | |
|---|---|---|---|---|
| 2008/0101665 A1* | 5/2008 | Collins | .................... | A61B 5/16 382/128 |
| 2008/0292194 A1* | 11/2008 | Schmidt | ................ | G06T 7/0012 382/217 |
| 2010/0027865 A1* | 2/2010 | Wels | .................... | G06K 9/4614 382/131 |
| 2011/0044524 A1* | 2/2011 | Wang | ..................... | G01R 33/54 382/131 |

* cited by examiner

METHOD OF ANALYZING MULTI-SEQUENCE MRI DATA FOR ANALYSING BRAIN ABNORMALITIES IN A SUBJECT

CROSS REFERENCE TO RELATED APPLICATIONS

This application is a 35 U.S.C. § 371 U.S. national entry of International Application PCT/US2013/033334, having an international filing date of Mar. 21, 2013, which claims the benefit of U.S. Provisional Application No. 61/613,569, filed Mar. 21, 2012, the content of each of the aforementioned applications is herein incorporated by reference in their entirety.

GOVERNMENT SUPPORT

This invention was made with government support under grant nos. NS070906, NS060910, and NS003119, awarded by the National Institutes of Health. The government has certain rights in the invention.

FIELD OF THE INVENTION

The present invention relates generally to medical imaging. More particularly the present invention relates to methods of analyzing brain abnormalities in a subject.

BACKGROUND OF THE INVENTION

Multiple sclerosis (MS) is an inflammatory disease of the brain and spinal cord characterized by demyelinating lesions that are most easily identified, at least on magnetic resonance imaging (MRI) studies, in the white matter of the brain. Quantitative analyses of MRI, such as the number and volume of lesions, are essential for evaluating disease-modifying therapies and monitoring disease progression. MRI measures are also a common primary endpoint in phase II immunomodulatory drug therapy trials. In practice, lesion burden is determined by visual examination and delineation of serial MRI. Manual delineation is challenging and time consuming, as three-dimensional information from several MRI modalities must be integrated. As manual assessment of MRI is also prone to large inter- and intra-observer variability, a sensitive and specific automated method to detect lesions in the brain is essential for the analysis of large MS studies.

One such study provides a comprehensive review of currently available automated cross-sectional MS lesion segmentation methods, or methods used to identify lesions from a single MRI study. These methods are divided into four categories: supervised classifier with an atlas, supervised classifier with no atlas, unsupervised classifier with an atlas, and unsupervised classifier with no atlas.

Supervised methods with atlases involve registering volumes to a statistical or topological atlas containing prior information about lesion location. Supervised classification methods are then applied to the volumes: artificial neural networks, k-nearest neighbors, fast trimmed likelihood estimator and hidden Markov chains, principal components analysis, Fisher linear discriminant and decision forests, and Bayes.

Supervised methods without atlases train on manually-segmented images annotated by experts and use image intensities of MRI to classify lesions. Supervised classification algorithms are applied to the volumes: artificial neural networks, spatial clustering, k-nearest neighbors, Parzen window, Parzen window and morphological gray scale reconstruction, Bayes, AdaBoost, simulated annealing and Markov random fields, and graph cuts.

Unsupervised methods with atlases involve registering volumes to a statistical or topological atlas and then applying unsupervised classification methods to the volumes: expectation maximization and Markov random fields, region partitioning, expectation maximization and Gaussian mixture models, and fuzzy C-means.

Unsupervised methods without atlases apply unsupervised classification methods to the volumes: fuzzy C-means, expectation maximization and constrained Gaussian mixture models, Bayes, adaptive mixtures method and Markov random fields, expectation maximization and mean shift, and expectation maximization.

Almost all of the aforementioned methods, use multi-modality MRI information to classify lesions. The most widely-used feature across all segmentation methods is voxel intensity, which derives strength from a multi-modality approach.

One difficulty in automated segmentation of MRI is due to variable imaging acquisition parameters. All of the aforementioned methods have tuning parameters that are adjusted to a particular data set and may not generalize to a new data set with different acquisition parameters. These parameters are not informed by the data and therefore must be tuned empirically, often with little to no interpretability of the parameter. Application to a new data set may require several iterations of segmentations to adjust the tuning parameters to values that produce acceptable segmentations. A method in which the tuning parameters are informed by the data and for which adjustments are intuitive and simple would therefore be valuable.

A second difficulty in intensity-based segmentation is that MRI data are acquired in arbitrary units; units can vary widely between and within imaging centers. These variations are attributed to scanner hardware, interactions between hardware and patients, and variations in acquisition parameters. Therefore, proper intensity normalization is essential in developing a robust segmentation method. Many of the segmentation methods use intensity-normalized images, but these methods do not demonstrate robustness of the normalization procedure to changes in imaging acquisition parameters and imaging centers.

A third difficulty is intensity inhomogeneity, the slow spatial intensity variations of the same tissue within an MRI volume. Inhomogeneity can significantly reduce the accuracy of image segmentation, and therefore some form of spatial normalization is necessary for accurate lesion segmentation. Most lesion segmentation methods assume that these inhomogeneities have been corrected during image preprocessing, while it has been found that strong spatial patterns within tissue type even after the N3 inhomogeneity correction algorithm is applied few researchers account for image inhomogeneities in their model.

It would therefore be advantageous to provide an easy to use, fully automated, robust, and novel statistical method for cross-sectional MS lesion segmentation. Using intensity information from multiple modalities of MRI, a logistic regression model assigns voxel-level probabilities of lesion presence.

SUMMARY

According to a first aspect of the present invention a method of analysis of multi-sequence MRI data for neurological disorders includes obtaining intensity information using an MRI modality and assigning a probability of a presence of a neurological abnormality using a logistic regression model. The method also includes producing results in the form of regression coefficients that can be applied to the multi-sequence MRI data and adjusting for intensity inhomogeneities. Additionally, the method includes providing a segmentation for identifying the neurological abnormality in a subject and locating a position of the neurological abnormality in the subject.

According to an embodiment of the present invention, the multi-sequence MRI data includes T1-weighted, T2-weighted, T2-weighted fluid attenuation inversion recovery (FLAIR), and PD-weighted images. The method further includes pre-processing said multi-sequence MRI data using standard image analysis tools and normalizing the multi-sequence MRI data using a normalization procedure. The method also includes sequentially blurring images comprising the multi-sequence MRI data using Gaussian blurs with varying kernel sizes. Another sequence of the method includes oversmoothing the images, maintaining regional features of the multi-sequence MRI data, as well as spatial inhomogeneities, and removing local voxel-specific features. Additionally, the method includes providing a multi-scale procedure, thereby allowing for different resolutions in terms of the regional features of interest wherein the neurological abnormalities are included in the blurred images.

In accordance with another aspect of the present invention a sequence of the method includes isolating probable abnormalities from each modality, each of the blurred images including in a logistic regression model having estimates of voxel-specific probability of the voxel being part of the abnormality in an interaction between the images and the blurred images, removing said abnormality from the image, reblurring said image, and providing a refined description of regional patterns including spatial inhomogeneity and inhomogenieity and underlying anatomy of said abnormalities. The method also includes using said more refined blurred images and said normalized data and the interactions between the images and the blurred images, refitting logistic regression model, refining estimates of said voxel-specific probability of said abnormality, directly interpreting said probabilities, and yielding binary segmentation maps. The abnormality can take the form of a brain lesion and the method can further include utilizing a single cross-sectional imaging study and identifying how much said lesion load said subject has and where in the brain said lesions exist. The abnormality can be associated with multiple sclerosis. Additionally, the method can include resampling said multi-sequence MRI data over time, reestimating coefficients and performance using partial ROC methods, and obtaining a robust analysis of the image data.

In accordance with another aspect of the present invention, a system for analysis of multi-sequence MRI data for neurological disorders includes an MRI imaging system configured to collect and transmit multi-sequence MRI data as well as images related to the neurological disorder. A data storage device is configured to store the multi-sequence MRI data and images related to the neurological disorder. Additionally, a computing device is configured to process the multi-sequence MRI data and images, wherein the computing device is further configured to provide a segmentation for identifying a neurological abnormality in a subject and locate a position of said abnormality in said subject.

In accordance with even another aspect of the present invention, a method of analysis of multi-sequence MRI data for neurological disorders includes creating a brain tissue mask using multi-sequence MRI data and normalizing MRI volumes for intensity. The method also includes constructing initial BLUR volumes using the brain tissue mask and the normalized MRI volumes and fitting an initial logistical regression model to the BLUR volumes. Additionally, the method includes performing lesion segmentation of any neurological abnormalities and constructing a final BLUR volume with any neurological abnormalities removed. The method includes fitting a final logistical regression model to the final BLUR volume, and creating a probability map and neurologic abnormality lesion segmentation.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention, referred to as Oasis is Automated Statistical Inference for Segmentation (OASIS), is a fully automated and robust statistical method for cross-sectional MS lesion segmentation. Using intensity information from multiple modalities of MRI, a logistic regression model assigns voxel-level probabilities of lesion presence. After training on manual segmentations, the OASIS model produces interpretable results in the form of regression coefficients that can be applied to imaging studies quickly and easily. OASIS uses intensity-normalized brain MRI volumes, enabling the model to be robust to changes in scanner and acquisition sequence. OASIS also adjusts for intensity inhomogeneities that preprocessing bias field correction procedures do not remove using Blur is a Local Uniform Representation (BLUR) volumes. This allows for more accurate segmentation of brain areas that are highly distorted by inhomogeneities, such as the cerebellum. One of the most practical properties of OASIS is that the method is fully transparent, easy to explain and implement, as well as simple to modify for new data sets.

Additionally, to illustrate the robustness of OASIS to imaging acquisition parameters, and to illustrate the present invention, the performance of the algorithm was evaluated on data from two separate imaging centers with varying acquisition parameters. This is a crucial criterion for assessing the generalizability and utility of the method. These performance evaluations are described in further detail, herein, below, with respect to the exemplary embodiment, in order to more fully illustrate the present invention.

Figure 1A:
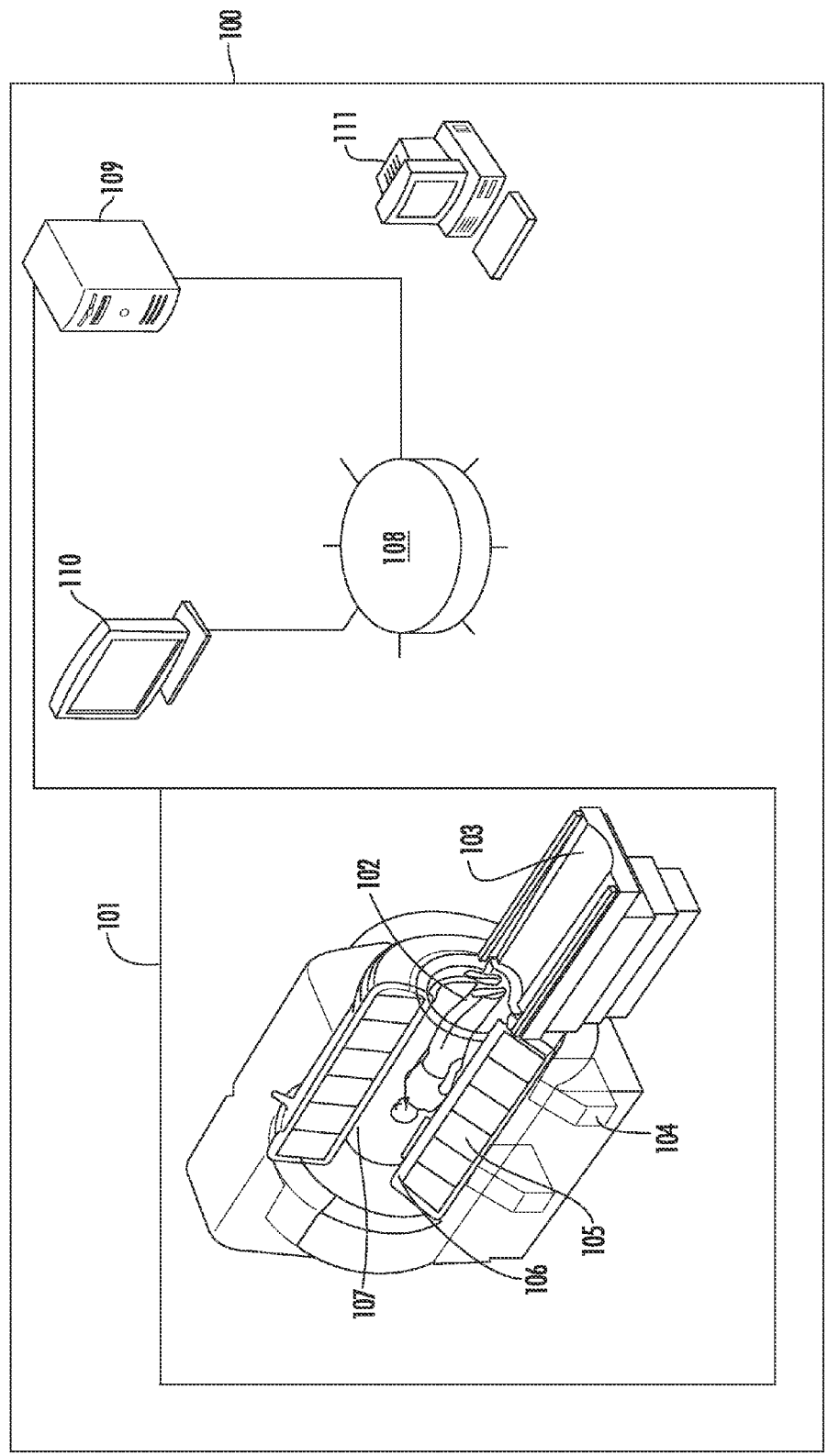
FIG. 1A is a schematic illustration of a magnetic resonance imaging (MRI) system 100 according to an embodiment of the current invention.

FIG. 1A is a schematic illustration of a magnetic resonance imaging (MRI) system 100 according to an embodiment of the current invention. Other embodiments of the current invention can include other types of imaging systems instead of, or in addition to, MRI systems.

The MRI system 100 includes a magnetic resonance scanner 101, capable of imaging a subject 102 under observation on scanner bed 103. Magnetic resonance scanner 101 is located on base 104 and has a main magnet 105, a gradient coil system 106, and a radio-frequency (RF) coil system 107. Main magnet 105 provides a substantially uniform main magnetic field BO for subject 102. Gradient system 106 provides a perturbation of the main magnetic field BO to encode spatial information of the constituent water molecules with a region of interest of subject 102 under observation. The spatial information can be a spatial distribution of magnetizations, for example. Radio-frequency (RF) coil system 107 transmits RF pulses into a region of interest of subject 102 under observation and receives magnetic resonance (MR) response signals from subject 102. The region of interest can be, but is not limited to, a brain, a heart, a lung, a liver, a kidney, or other organs of interest in the thoracic or abdominal cavities, muscle or other tissue.

RF coil system 107 comprises at least one radio frequency (RF) coil configured to irradiate a radio frequency (RF) pulse into a region of interest of the subject 108. The RF coil can be, for example, a surface coil, a neck coil, an extremity coil, a head coil, a body, a phased-array coil, etc. The RF coil can be embodied as a solenoid, a planar coil, a volume coil, a quadrature coil, or variations thereof. The RF coil can be for transmission only or for both transmission and reception. RF coil system 107 can further comprise a power amplifier to amplify the RF pulse being transmitted or the received magnetic resonance signals. The power amplifier can be programmed or configured to amplify at more than one level of amplification. RF coil system 107 can further comprise matching and/or tuning networks for impedance matching and/or frequency tuning purposes.

The MRI system 100 can further include a data storage unit 108 and a signal processing unit 109. Data storage unit 108 is in communication with signal processing unit 109 to store signals from the region of interest of subject 102 under observation. The subject may be, for example, a human, an animal, a phantom, a sample, or combinations thereof. The region of interest may be, for example, a brain, a heart, a muscle, a liver, a kidney, a knee, a neck, etc.

Data storage unit 108 can be, for example, a hard disk drive, a network area storage (NAS) device, a redundant array of independent disks (RAID), a flash drive, an optical disk, a magnetic tape, a magneto-optical disk, etc. However, the data storage unit 108 is not limited to these particular examples. It can include other existing or future developed data storage devices without departing from the scope of the current invention.

Signal processing unit 109 is in communication with magnetic resonance scanner 101 to receive magnetic resonance signals from the region of interest in response to the RF pulse. Signal processing unit 109 can be partially or totally incorporated within a structure housing magnetic resonance scanner 101. Signal processing unit 109 can be at least partially incorporated in a workstation that is structurally separate from and in communication with magnetic resonance scanner 101. A workstation can be a computer having at least one central processing unit (CPU) and one memory, for example, static random access memory (SRAM), dynamic random access memory (DRAM), erasable programmable random access memory (EPROM), non-volatile flash memory, etc. Alternately, signal processing can be done at a remote computer or terminal, and the MRI system 100 can be networked either via hardwiring or a wireless system to a separate CPU or server configured to execute any signal processing or other computing needs related to the MRI system 100. The CPU can also be used to execute the method of the present invention described herein. The CPU can be integrated with the MRI system 100 or can be networked to the MRI system 100 either wirelessly or via a hardwired connection. The CPU can also take the form of a server or other computing device and can be on-site or off-site.

Signal processing unit 109 can be configured to reconstruct a plurality of images of the region of interest of the subject 108 based on the received RF response signals. Signal processing unit 109 can be further configure to retrieve stored signals and process the signals according to embodiments of the current invention that will be described in more detail below.

Output from signal processing unit 109 can be rendered on a display device, such as, for example, viewing station 110 or a console station 111. Viewing station 110 or console station 111 may be, for example, a cathode ray tube (CRT) monitor, a liquid crystal display (LCD) monitor, a digital light projection (DLP) monitor, a plasma screen, an organic light emitting diode (OLED), etc. The processed results may be used for further analysis and diagnosis.

EXAMPLE

An exemplary implementation of the present invention is described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

2. Materials and Methods

Figure 1B:
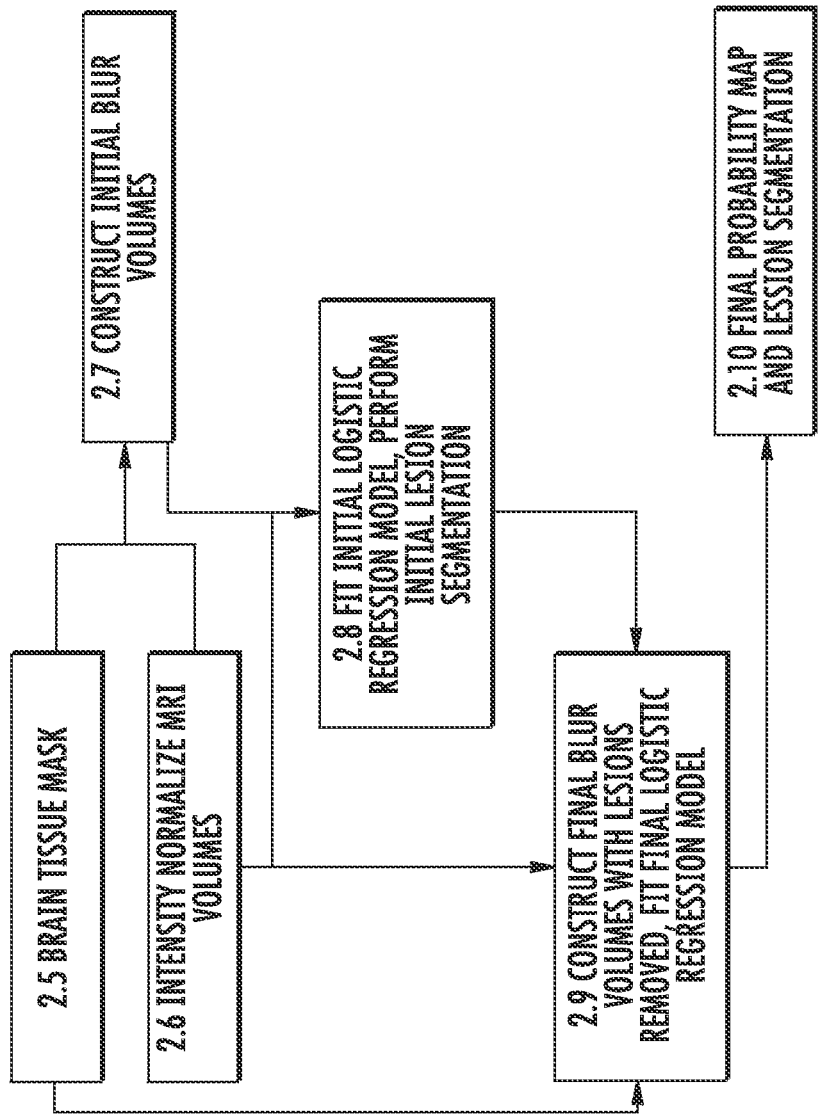
FIG. 1B illustrates a flowchart outline of the OASIS method, with numbered boxes corresponding to the subsections of the Materials and Methods Section, according to an embodiment of the present invention.

OASIS is a method inspired by Subtraction Based Inference for Modeling and Estimation (SuBLIME), an automated method for the longitudinal segmentation of incident and enlarging MS lesions described in International Application No. PCT/US2012/067997, and incorporated herein, by reference. Before the OASIS logistic regression model is fit, a brain tissue mask is created, all MRI volumes are intensity normalized, and BLUR volumes are created to capture local spatial information and adjust for remaining field inhomogeneities. The OASIS method involves two iterations of model fitting: the first to perform an initial lesion segmentation and a second using this initial lesion segmentation to remove lesions, which can distort the BLUR volumes. After the final model is fit, the regression coefficients are applied to produce three dimensional maps of voxel-level probabilities of lesion presence. FIG. 1B illustrates a flowchart outline of the OASIS method, with numbered boxes corresponding to the steps of the methods as well as corresponding to the subsections of the description below.

The performance of OASIS on MRI volumes of the brain acquired with various acquisition protocols is evaluated. Data sets from two different imaging centers are used for validation, which are referred to as Validation Set 1 and Validation Set 2. Validation Set 1 has manual lesion segmentations. The OASIS method is trained on a subset of the studies in this dataset, and tested on the remaining studies. Validation Set 2 is used to demonstrate robustness to image acquisition parameters. The coefficients from the model trained on Validation Set 1 are applied to the studies in Validation Set 2 and experts can be used to evaluate the OASIS lesion segmentations.

2.1 Study Population

Validation Set 1 contains a total of 131 MRI studies from 131 subjects. Of these studies, 98 are from patients with MS and 33 are healthy volunteer scans. Of the 98 patients with MS, the median age is 44 years, 72 are female (26 male), and the median EDSS is 3.5. The median age of the healthy volunteers is 34 and 19 are female (14 male).

Validation Set 2 contains a total of 169 MRI studies from 149 subjects. Twenty subjects in Validation Set 2 have baseline and follow-up scans. The subjects in the validation set are a mixture of healthy volunteers and disease patients: 110 of the patients have MS, 38 have other neurological diseases, and one is a healthy volunteer. The median age of the MS patients is 42, 54 are female (56 male); 68 have Relapsing Remitting MS, 31 have Primary Progressive MS, and 11 have Secondary Progressive MS. The median age of the patients with other neurological diseases is 41 years, and 8 are female (30 male). The healthy volunteer is a 28 year old female.

2.2 Experimental Methods

T1-weighted, T2-weighted, fluid-attenuated inversion recovery (FLAIR) and proton density (PD) volumes were acquired for all subjects at each study and all imaging protocols were approved by local institutional review boards. For Validation Set 1, T1-MPRAGE images (repetition time (TR)=10 ms; echo time (TE)=6 ms; flip angle (FA) $\alpha=8°$; inversion time (T1)=835 ms, in-plane resolution=1.1 mm×1.1 mm; slice thickness=1.1 mm), 2D T2-weighted pre-contrast FLAIR images (TR=11000 ms; TE=68 ms; T1=2800 ms; in-plane resolution=0.83 mm×0.83 mm; slice thickness=2.2 mm), T2-weighted images and PD images (TR=4200 ms; TE=12 ms; in-plane resolution=0.83 mm×0.83 mm; slice thickness=2.2 mm) were acquired on a 3 tesla MRI scanner (Philips Medical Systems, Best, The Netherlands).

For Validation Set 2, the 3D T2-weighted post-contrast FLAIR, PD, and T2-weighted volumes were acquired using a 2D dual-echo fast-spin-echo sequence and the 3D T1-weighted MPRAGE volume using a gradient-echo sequence. The PD and T2-weighted volumes were acquired as short and long echoes from the same sequence. Typical scanning parameters were used for the different studies and these studies were acquired on a single 3 tesla MRI scanner (Signa Excite HDxt; GE Healthcare, Milwaukee, Wis.).

2.3 Image Preprocessing

Before building the statistical model for the lesion segmentation, the images are preprocessed from Validation Set 1 and Validation Set 2 using the tools provided in Medical Image Processing Analysis and Visualization (MIPAV), TOADS-CRUISE (http://www.nitrc.org/projects/toads-cruise/), and Java Image Science Toolkit (JIST) software packages. The T1-weighted image of each subject into the Montreal Neurological Institute (MNI) standard space (voxel resolution 1 mm$^3$) is rigidly aligned. Then the FLAIR, PD, and T2-weighted images of each subject are registered to the aligned T1-weighted images. The N3 inhomogeneity correction algorithm is also applied to all images and removed extracerebral voxels using SPECTRE, a skull-stripping procedure.

2.4 Statistical Modeling and Spatial Smoothing

All statistical modeling is performed in the R environment (version 2.12.0, R Foundation for Statistical Computing, Vienna, Austria) with the packages AnalyzeFMRI, biglm, ff, and ROCR. The FSL tool fslmaths (http://www.fmrib.ox.ac.uk/fsl) is used for the three dimensional spatial smoothing of the BLUR volumes.

2.5 Brain Tissue Mask

Figures 2A, 2B, 2C, 2D, 2E, 2F, 2G:
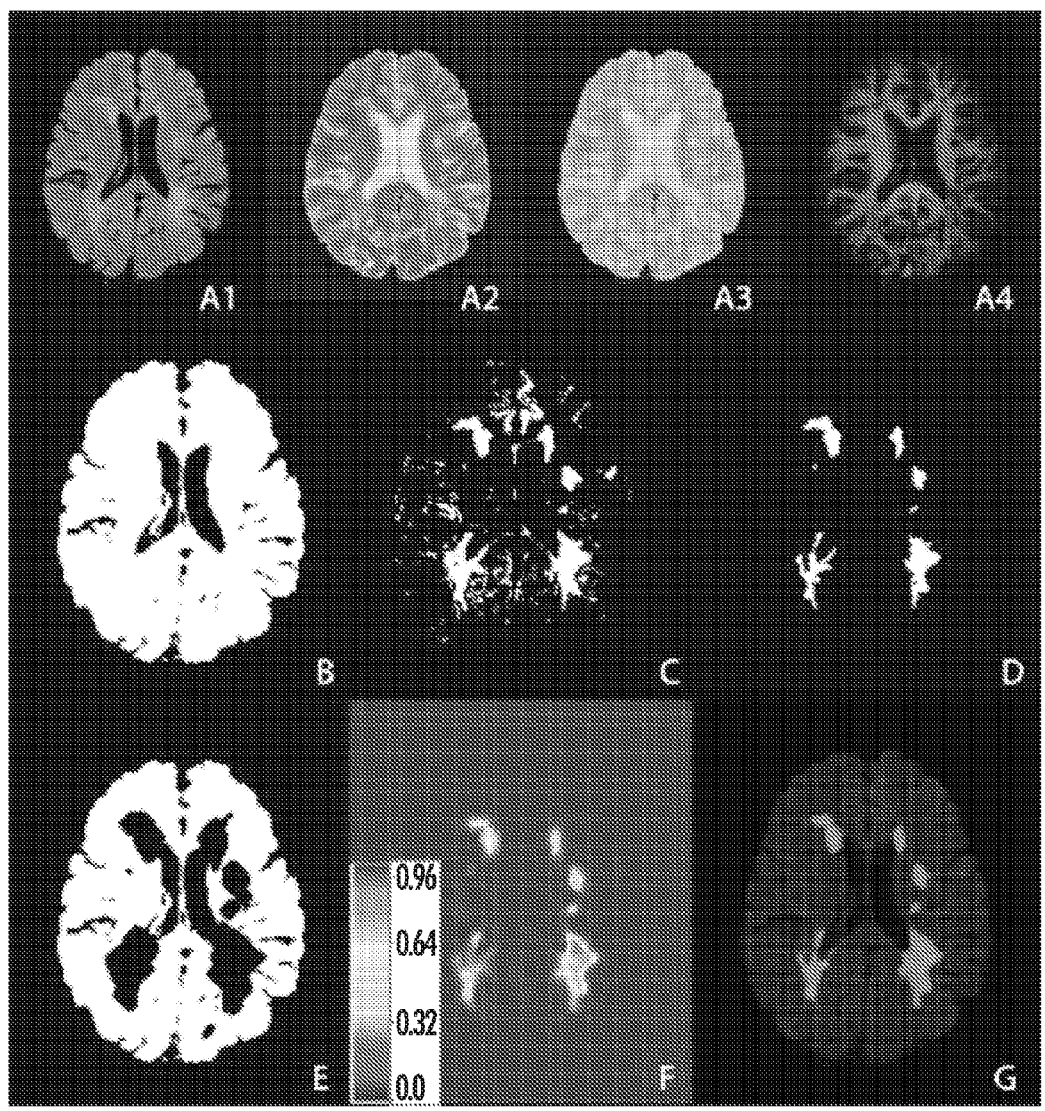
FIG. 2A shows a slice of the normalized images from all four modalities from a single subject with MS: FLAIR, T2-weighted, PD, and T1-weighted, according to an embodiment of the present invention.
FIG. 2B shows a slice of the brain tissue mask for a particular subject for illustration according to an embodiment of the present invention.
FIG. 2C shows a slice of the voxel selection mask for a single subject, according to an embodiment of the present invention.
FIG. 2D is an example of manual lesion segmentation, which is an appropriate gold standard measure for the OASIS model, according to an embodiment of the present invention.
FIG. 2E shows the brain tissue mask with the lesions removed, according to an embodiment of the present invention.
FIG. 2F shows a slice of the probability map for a subject and a scale of intensities. according to an embodiment of the present invention.
FIG. 2G shows a slice of a hard segmentation overlaid on the FLAIR image for a subject, according to an embodiment of the present invention.

The first step in OASIS is to create a mask of the brain that excludes cerebrospinal fluid (CSF). CSF is excluded because it disrupts the capture of the inhomogeneity field and distorts the representation of the local cerebral features when creating BLUR volumes. To make this mask, the extracerebral voxel removal mask described in the Image Preprocessing Section is used and voxels in the mask that appear hypointense in the FLAIR volume are excluded. Because CSF is hypointense in the FLAIR, empirically, it is found that excluding voxels falling below the bottom 15th percentile of FLAIR intensities over the extracerebral voxel removal mask removes CSF outside of the brain and in the ventricles. This mask is referred to as the brain tissue mask. FIG. 2B shows a slice of the brain tissue mask for a particular subject for illustration.

2.6 Intensity Normalization

Intensities from the FLAIR, PD, T2-weighted, and T1-weighted volumes are used to identify the presence of MS lesions. The observed intensity of voxel v, for subject i is denoted by:

$$M_i^0(v), M=FLAIR, PD, T_2, T_1$$

where M indicates the imaging sequence.

MRI volumes are acquired in arbitrary units. Analyzing images across subjects and imaging centers requires that images be normalized so that voxel intensities have common interpretations.

One study proposed a normalization approach with respect to a mask of the subject's normal-appearing white matter (NAWM). Because the method is normalizing for lesion segmentation, a mask of the NAWM is not needed for this preliminary step. However, this normalization approach has been adapted to normalization with respect to the brain tissue mask. The normalized intensity of voxel v, for subject i is denoted by:

$$M_i^N(v) = \frac{M_i^0(v) - \mu_{i,M}^0}{\sigma_{i,M}^0}$$

where $\mu_{i,M}^0$ and $\sigma_{i,M}^0$ are the mean and standard deviation of the observed voxel intensities in the brain tissue mask of subject i, from sequence M. The normalized voxel intensities, $\mu_i^N(v)$, are deviation measures from the mean intensity of the brain tissue mask for a particular subject and imaging modality, expressed in standard deviation units of the brain tissue mask. This enables modeling at the population level, where measurements now have the same interpretation across subjects and visits. The procedure was found to be robust to acquisition parameters, as well. FIG. 2A shows a slice of the normalized images from all four modalities from a single subject with MS: FLAIR, T2-weighted, PD, and T1-weighted.

2.7 Blur is a Local Uniform Representation Volumes

Intensity inhomogeneity can significantly reduce image segmentation accuracy. Inhomogeneities of a voxel Y are commonly modeled as Y=αX+β, where X is the true voxel intensity, α is the multiplicative inhomogeneity field and β represents additive noise. There are a number of different approaches for estimating the intensity inhomogeneity field α. This field can be estimated through phantom studies, theoretical models, or retrospectively from imaging data. Another study provides a comprehensive review of retrospective methods, concluding that no method is uniformly better than the others.

Figure 3:
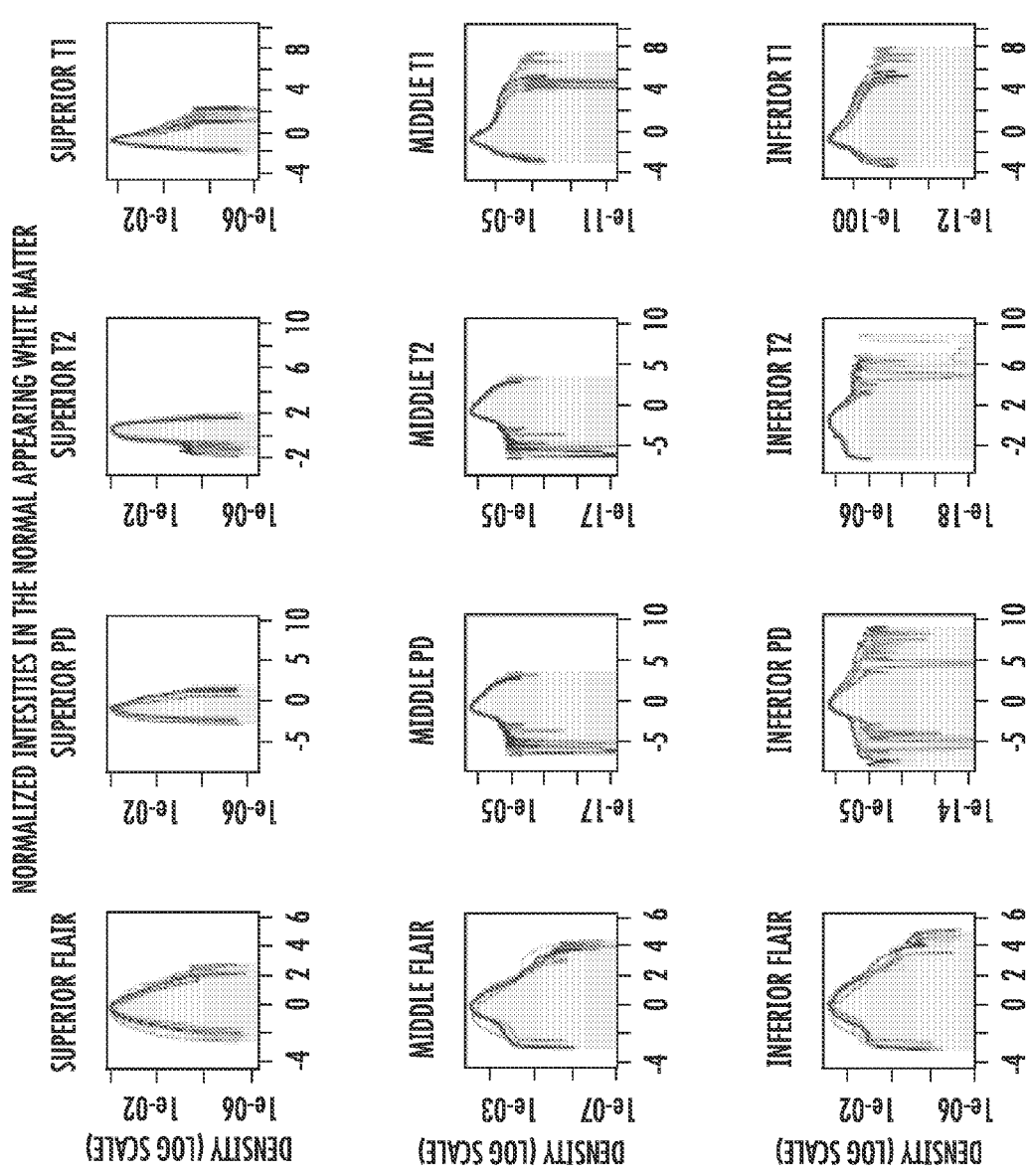
FIG. 3 shows a histogram of the intensities in a mask of the NAWM produced by LesionTOADs for the superior, middle, and inferior parts of the brain for N3 corrected and intensity-normalized FLAIR, PD, T2-weighted, and T1-weighted volumes from five randomly selected subjects from Validation Set 1, according to an embodiment of the present invention.

Even after N3 inhomogeneity correction it is found that there remains intensity variations in the same tissue class within an MRI volume. In Validation Set 1, this variation increased when moving from the superior to inferior parts of the brain. FIG. 3 shows a histogram of the intensities in a mask of the NAWM produced by LesionTOADs for the superior, middle, and inferior parts of the brain for N3 corrected and intensity-normalized FLAIR, PD, T2-weighted, and T1-weighted volumes from five randomly selected subjects from Validation Set 1. The LesionTOADs tissue segmentations is used for initial data exploration. The superior of the brain, based on axial slices in MNI space, is defined to be the vertex, including the centrum semiovale and portions of the frontal and parietal cortex, the middle of the brain to be the level of the lateral and third ventricles, including the superior temporal lobes and superior midbrain, and the inferior of the brain to be the inferior temporal lobes, the brainstem, and the cerebellum. In the five randomly sampled subjects from Validation Set 1, the variability of the intensities in the inferior part of the brain is much larger than those in the superior part of the brain across all imaging modalities. The intensity distributions in the inferior of the brain are also right-skewed for all modalities; there are intensities in the NAWM of the inferior part of the brain that are much higher than intensities found in NAWM of the middle or superior part of the brain. These inhomogeneities are subtle, cannot be observed by direct inspection of N3 corrected images, and are likely responsible for serious inaccuracies in algorithms that rely on the assumption that intensities are spatially normalized.

To account for this intensity inhomogeneity a sequence of multi-resolution BLUR volumes, obtained using different levels of smoothing, are used. BLUR volumes are created by three dimensional smoothing of the normalized volume from each modality over the brain tissue mask. A Gaussian blur with relatively large kernel window size is used to smooth over the features in the brain and capture the pattern of the remaining inhomogeneity. Recall that the brain tissue mask excludes the CSF. The CSF, especially in the ventricles, is a large feature that is hyperintense in the T2-weighted and PD volume and hypointense in the T1 weighted and FLAIR volumes. If CSF were included in the mask it would misrepresent the local cerebral features and field around the ventricles and near the outer edge of the brain.

Figure 4:
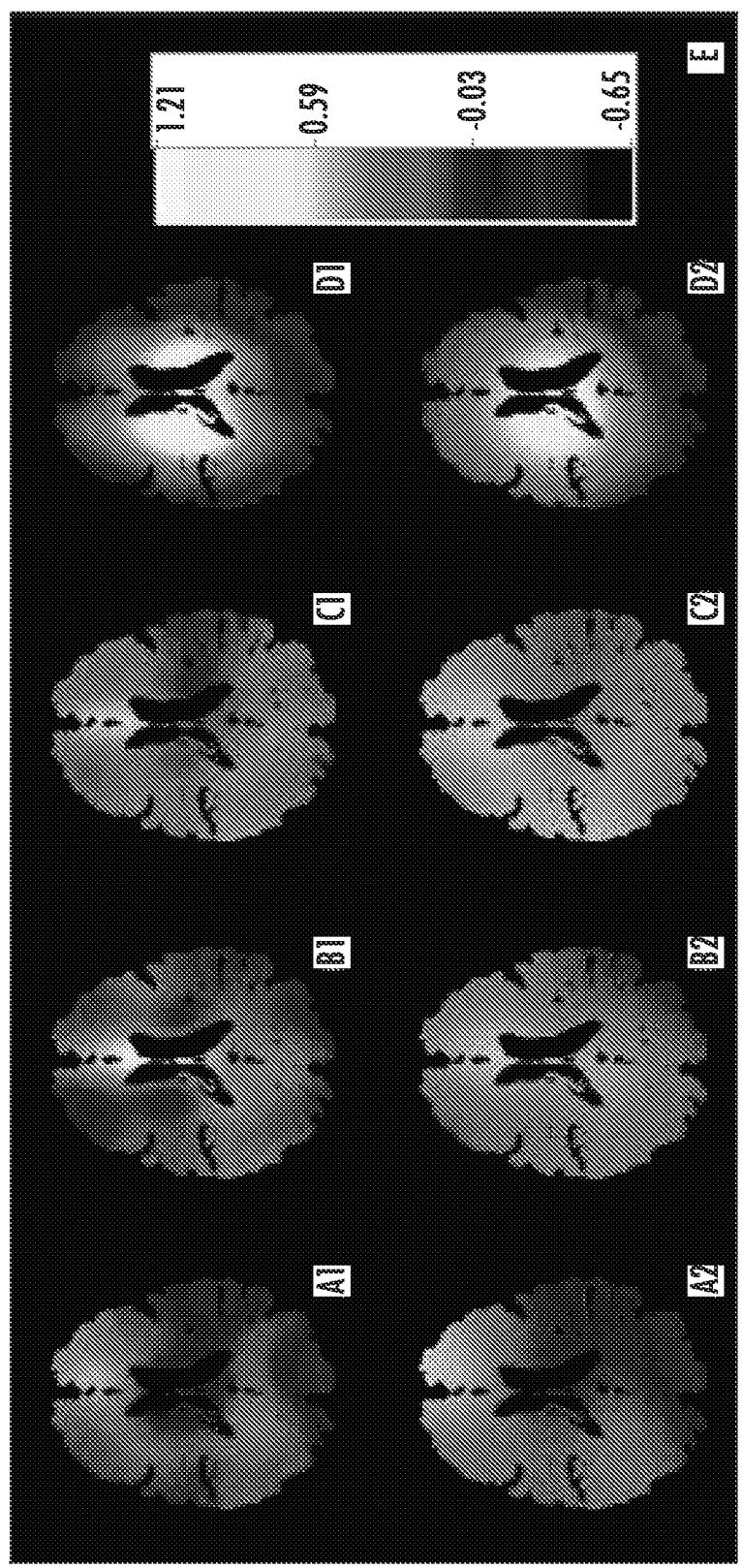
FIG. 4 shows the BLUR volumes for both kernel window sizes of 10 and 20 from each modality, according to an embodiment of the present invention.

For subject i and imaging modality M, let k be the size of the kernel window. Then the intensity in voxel v of the BLUR volume of imaging modality M is expressed as $GM_i^N(v,k)$. The BLUR volumes are used in the OASIS model to incorporate spatial information and to account for inhomogeneities in the brain that persist after N3 correction. For OASIS BLUR volumes are used as covariates with kernel window sizes of 10 and 20 voxels, which were found empirically on Validation Set 1 to work well. FIG. 4 shows the BLUR volumes for both kernel window sizes of 10 and 20 from each modality. The kernel window size of 20 smooths over the anatomical features almost completely, while the kernel window size of 10 still preserves some of these features, such as the hyperintesities of the grey matter in the FLAIR, T2-weighted, and PD volumes and hyperintensities of the grey matter in the T1-weighted volume.

2.8 Oasis is Automated Statistical Inference for Segmentation

OASIS uses logistic regression to model the probability that a voxel is part of a lesion. Logistic regression is used because it is extremely simple and easy to interpret. The model lesions at the voxel level are chosen using FLAIR, PD, T2-weighted, and T1-weighted intensities as well as the intensities from the BLUR volumes of each modality with kernel window sizes of 10 and 20 voxels. The model must be trained on a gold standard measure of lesion presence. FIG. 2D is an example of manual lesion segmentation, which is an appropriate gold standard measure for the OASIS model. The result of the model is a collection of coefficients that can be used to create three dimensional maps of the probabilities of lesion presence. OASIS obtains the estimated logit of the probability of each voxel being part of a lesion by weighting these 12 images (the four imaging modalities and BLUR volumes for each modality) with the coefficients. These coefficients are explicit, obtained using standard model fitting techniques, and can be re-used in other imaging studies. If a different imaging study contains a subset of gold standard lesion segmentations then OASIS can quickly re-fit these coefficients and provide automatic segmentations for hundreds of studies.

The first step of the modeling procedure is to select candidate voxels to minimize false positives and computation time. Lesions appear as hyperintensities in the FLAIR volume. The brain tissue mask was applied to the FLAIR volume and the 85th percentile and above of voxels in the brain tissue mask were selected as candidate voxels for lesion presence. In Validation Set 1, there were a total of 1,093,394 lesion voxels (a volume of 1,093 cm$^3$). The voxel selection procedure excluded 64,556 (6%) of these voxels, but lowered the searchable area to 15% of the original size, diminishing the number of potential false positive voxels. FIG. 2C shows a slice of the voxel selection mask for a single subject.

A voxel-level logistic regression model is then fit over the candidate voxels. In the OASIS model, the probability that a voxel is part of a lesion is represented as $P\{L_i(v)=1\}$, where L is a random variable denoting voxel-level lesion presence. If there is a lesion in voxel v for subject i, then $L_i(v)=1$. Otherwise, $L_i(v)=0$. The probability that a voxel v contains lesion incidence is modeled with the following logistic regression model:

geneities are thought to be multiplicative, so the interactions between the normalized volume and the BLUR volume in the model are used.

An advantage of the OASIS model framework is the interpretability of the coefficients. The coefficients for each modality are the log odds ratios of lesion presence for a voxel corresponding to an increased intensity of one normalized unit, given that both BLUR volumes for the modality are equal to zero, fixing all other predictors. The coefficients for each BLUR volume modality are the log odds ratios of lesion presence for a voxel corresponding to an increased intensity of one normalized unit, given that the modality is equal to zero, fixing all other predictors. The coefficients for the interaction terms are the additive effects for a one unit increase in a modality when the BLUR volumes for that modality are nonzero. This model is easy to adjust if additional predictors, modalities, or data features are found to be relevant to lesion segmentation.

2.9 OASIS Model Refinement

The second iteration of the OASIS model fitting is done to reduce the influence of lesions in the BLUR volumes. First, the model is fit and the estimated coefficients are used to create maps of the estimated probability of lesion presence at each voxel. To incorporate spatial information of the neighboring voxels and reduce noise, the estimated probabilities from the model are smoothed using a Gaussian kernel with window size of 3 mm. This kernel size is empirically chosen and found to perform well. The resulting probability maps are then thresholded using a liberal false positive rate of 1%, which results in model based hard segmentations of lesions. These lesions masks are then dilated by 5 voxels to ensure that the entire lesion is captured and removed from the brain tissue mask. FIG. 2E shows the brain tissue mask with the lesions removed. New BLUR volumes are created by applying a Gaussian blur of kernel window sizes of 10 and 20 to the normalized image from each modality over the brain tissue mask with the lesions removed. The BLUR volumes are inpainted to fill the places $$\begin{aligned}
l_{ogit}[P(L_i(v)=1)] = \ & \beta_0 + \\
& \beta_1 FLAIR_i^N(v) + && \beta_2 \mathcal{G}FLAIR_i^N(v,10) + && \beta_3 \mathcal{G}FLAIR_i^N(v,20) + \\
& \beta_4 PD_i^N(v) + && \beta_5 \mathcal{G}PD_i^N(v,10) + && \beta_6 \mathcal{G}PD_i^N(v,20) + \\
& \beta_7 T2_i^N(v) + && \beta_8 \mathcal{G}T2_i^N(v,10) + && \beta_9 \mathcal{G}T2_i^N(v,20) + \\
& \beta_{10} T1_i^N(v) + && \beta_{11} \mathcal{G}T1_i^N(v,10) + && \beta_{12} \mathcal{G}T1_i^N(v,20) + \\
& && \beta_{13} FLAIR_i^N(v) * \mathcal{G}FLAIR_i^N(v,10) + && \beta_{14} FLAIR_i^N(v) * \mathcal{G}FLAIR_i^N(v,20) + \\
& && \beta_{15} PD_i^N(v) * \mathcal{G}PD_i^N(v,10) + && \beta_{16} PD_i^N(v) * \mathcal{G}PD_i^N(v,20) + \\
& && \beta_{17} T2_i^N(v) * \mathcal{G}T2_i^N(v,10) + && \beta_{18} T2_i^N(v) * \mathcal{G}T2_i^N(v,20) + \\
& && \beta_{19} T1_i^N(v) * \mathcal{G}T1_i^N(v,10) + && \beta_{20} T1_i^N(v) * \mathcal{G}T1_i^N(v,20)
\end{aligned} \qquad [1]$$

The model is organized as a matrix with nine rows and three columns, containing a total of 20 predictors. The second through fifth rows contain the intensity information from the FLAIR, PD, T2-weighted and T1-weighted volumes, respectively. The predictors in the first column of the model are the normalized intensities of each modality, the second column BLUR volumes with a kernel window size of 10 and the third column BLUR volumes with a kernel window size of 20. The sixth through ninth rows contain the interactions between the normalized volumes and the BLUR volumes for the FLAIR, PD, T2-weighted and T1-weighted volumes respectively. The effect of magnetic field inhomowhere lesions were removed with the values expected in this area if it were occupied by normal, healthy tissue.

Figures 5A, 5B, 5C, 5D:
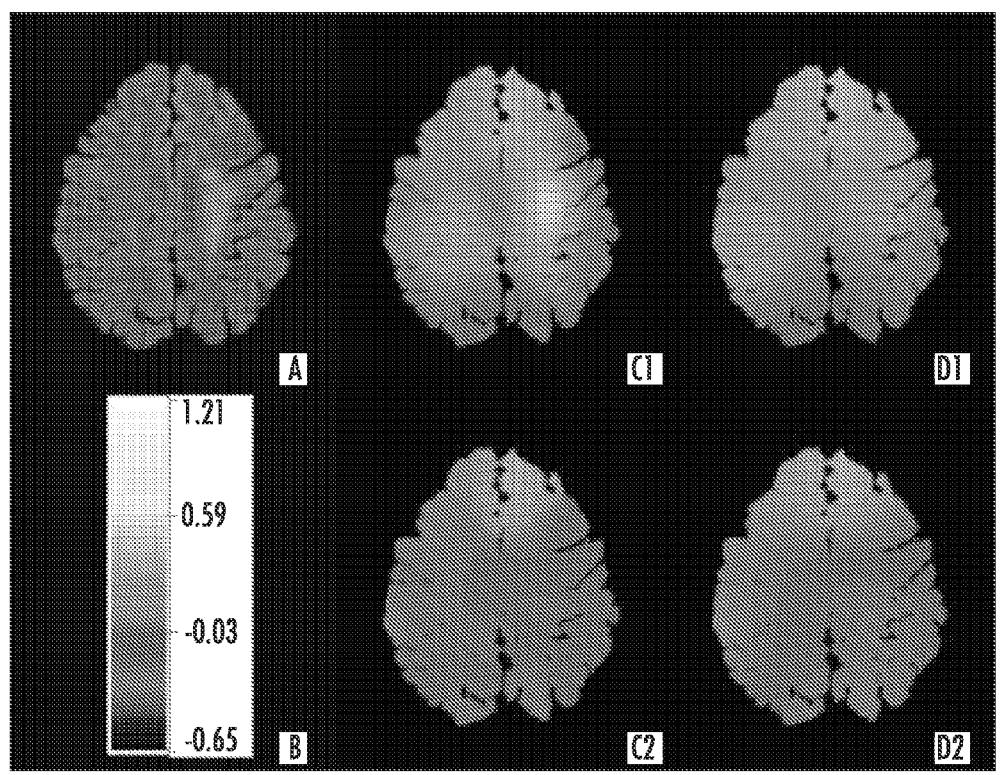
FIGS. 5A-5D show an axial slice for a subject of the FLAIR volume and the BLUR volume for this image with kernel window sizes of 10 and 20 before and after the lesions were removed, according to an embodiment of the present invention.

The intensity in voxel v of the normalized image after the second Gaussian blur has been applied is labeled as, $G_2 M_i^N$ (v,k). FIGS. 5A-5D show an axial slice for a subject of the FLAIR volume and the BLUR volume for this image with kernel window sizes of 10 and 20 before and after the lesions were removed. To link the figure with the notation, FIG. 5A shows $FLAIR_i^N(v)$, FIG. 5B shows a scale of intensities in the BLUR volumes, FIG. 5C1 shows $GFLAIR_i^N(v, 10)$, FIG. 5C2 shows $G^2 FLAIR_i^N(v, 10)$, FIG. 5D1 shows $GFLAIR_i^N(v, 20)$, and FIG. 5D2 shows $G^2 FLAIR_i^N(v, 20)$. The lesions are captured in the first BLUR volume, especially with the kernel size of 10, but are not captured in the second BLUR volume. The model [1] is refit over the same voxels using the second BLUR volume to obtain the final coefficients that are used to create the final probability maps. Again, the final estimated probabilities are smoothed using a Gaussian kernel with window size of 3 mm. FIG. 2F shows a slice of the probability map for a subject and a scale of intensities. Red indicates areas with a higher probability of being a lesion and blue indicates areas with a lower probability of being a lesion.

2.10 Probability Map and Binary Segmentation

Figure 6:
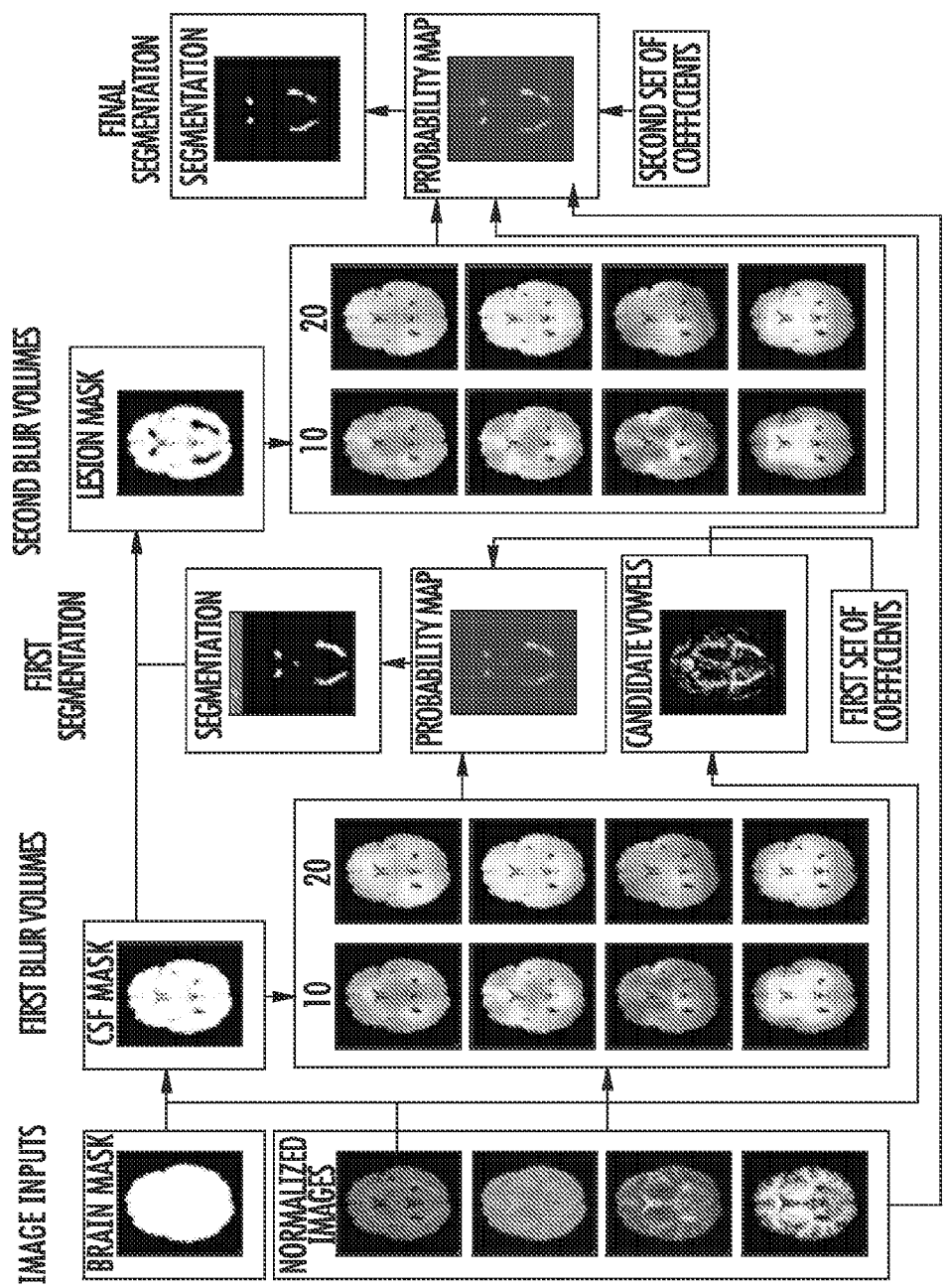
FIG. 6 is a flow chart describing a process of Gaussian smoothing, according to an embodiment of the present invention.

Using this fitted model to generate a probability map for the entire brain from a set of new images takes about 30 minutes for each study using a standard workstation. The Gaussian smoothing is the slowest step of the algorithm and takes approximately one minute for each volume. These computations can be parallelized to take substantially less time; the entire algorithm can be run in approximately 5 minutes with 8 cores. FIG. 6 is a flow chart describing this process. To make a probability map for a new study, the two sets of regression coefficients, a brain mask, and the FLAIR, PD, T2-weighted, and T1-weighted volumes are required. Using population-level thresholds, the probability maps from OASIS can be used to create hard segmentations of lesion presence. FIG. 2G shows a slice of a hard segmentation overlaid on the FLAIR image for a subject.

3 Experimental Results

It is difficult to compare the performance of MS lesion segmentation algorithms. Currently, there is no common open source database with gold standard lesion segmentations for training and testing algorithms. Synthetic MRI data, such as the simulated PD, T1-weighted, and T2-weighted volumes from BrainWeb, are often used for comparisons. But, algorithms that are correctly tuned for synthetic data may not be successful when applied to real acquired volumes.

To evaluate the performance of OASIS, data from Validation Set 1 is trained and validated and also data from Validation Set 2 is validated, using a set of studies acquired at a separate imaging center. This is done to evaluate how OASIS generalizes to a different scanning environment. The extrapolation of study results from one population to another may not be appropriate if they are different from the study population with regard to factors that inuence test accuracy. This is known as extrapolation bias. Validating an algorithm on the same data that it was trained on does not predict how the algorithm will perform when used on another data set. For example if the scanning parameters or hardware change, these factors may influence the accuracy of a segmentation method. To avoid extrapolation bias, the OASIS method is validated on both Validation Set 1 and Validation Set 2.

For the studies in Validation Set 1 gold standard manual lesion segmentations are used. For the studies in Validation Set 2, gold standard segmentations were not available. To evaluate the performance of OASIS on Validation Set 2, three experts (a neuroradiologist, neurologist, and radiologist) compared OASIS segmentations to those from Lesion-TOADS, an open-source lesion segmentation software.

3.1 Validation Set 1: Training with Gold Standard

Validation Set 1, described in detail in the Materials section, consists of 131 MRI studies: 98 studies from MS subjects and 33 studies from healthy subjects. To fit the model and to measure performance, a set of data is required in which the outcome is assessed using a gold standard measure. The gold standard was obtained using manual segmentation by a technologist with more than 10 years of experience in delineating white matter lesions. The segmentations were made from the FLAIR and T1-weighted volumes. FIG. 2C shows a manually segmented slice for a subject. The mean volume of lesions for MS subjects in Validation Set 1 is 11.2 cm3 (IQR: [1.7 $cm^3$, 16.6 $cm^3$]). It was assumed that the healthy subjects did not have any lesions.

To evaluate performance of the model within Validation Set 1, the model [1] is trained on 20 randomly selected subjects (15 MS subjects and 5 healthy subjects) and tested on the remaining 111 subjects (83 MS subjects and 28 healthy subjects). Only the studies from the 111 subjects are used in this test set to estimate the voxel-level receiver operator characteristic (ROC) curve and area under the curve (AUC). These performance measures are known to be susceptible to instability. To account for this, the subjects are nonparametrically bootstrapped with replacement to the training and testing sets. The model is then fit on the training set and the performance of the model is observed in the testing set. The OASIS model has an estimated AUC of 98% (95% CI; [96%, 99%]) in the test set.

Figure 7:
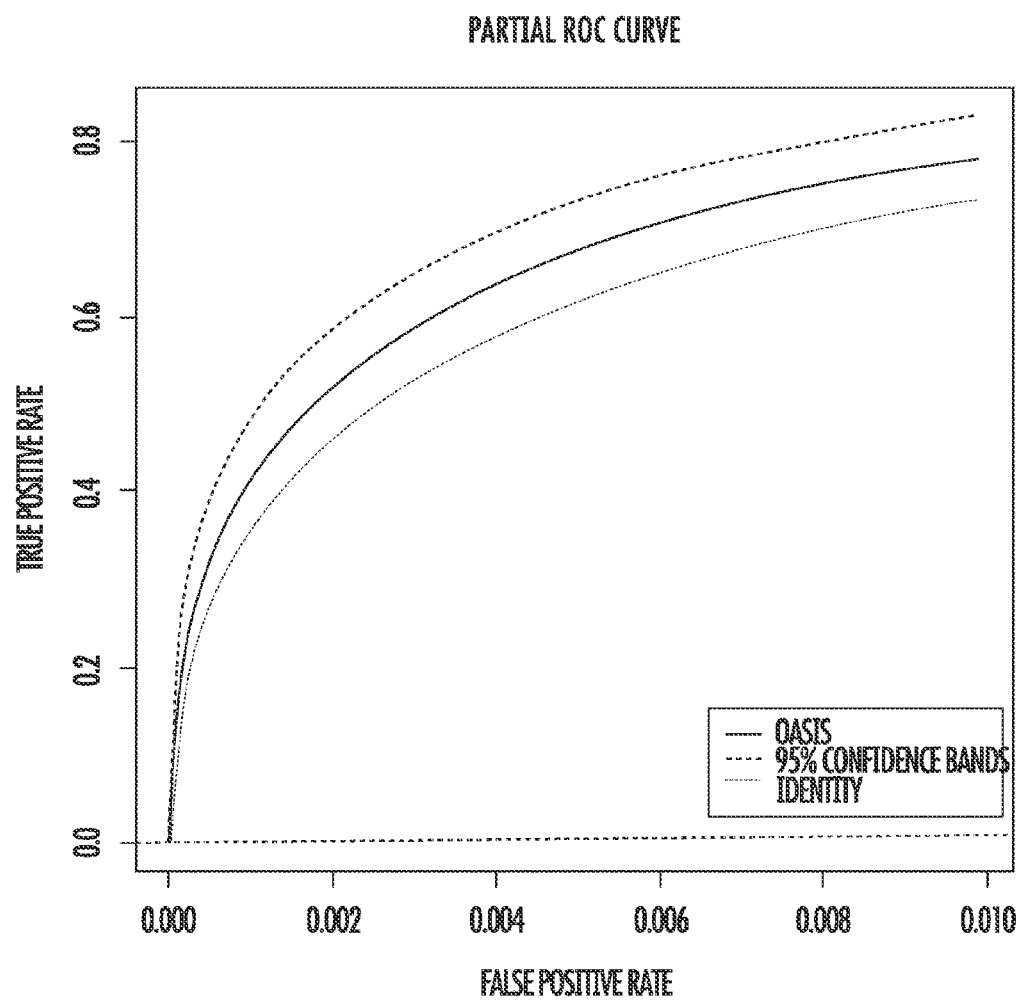
FIG. 7 shows the voxel level partial ROC curve for the test set with bootstrapped 95% confidence bands for clinically relevant false positive rates of 1% and below, according to an embodiment of the present invention.

It is known that the full AUC summarizes test performance over regions of the ROC space that are not clinically relevant for lesion segmentation. FIG. 7 shows the voxel level partial ROC curve for the test set with bootstrapped 95% confidence bands for clinically relevant false positive rates of 1% and below. The vertical axis of the partial ROC curve shows the true positive rate (sensitivity) for a given threshold of the probability map and the horizontal axis shows the false positive rate (1−specificity) for this threshold.

The coefficients from fitting the logistic model [1] over all 131 studies in Validation Set 1, a total of 24 million voxels, are reported in Table 1, below. The coefficients from the first and second fit of the model are provided. The variation in the coefficients is also assessed using the nonparametric bootstrap. The mean and IQR for the bootstrapped coefficients are also reported in Table 1. The variance of these coefficients is large in comparison to the estimates of the coefficients. The instability in the coefficients does not impact the performance of OASIS, as illustrated in the stability of the partial ROC curve.

TABLE 1

Regression coefficients from first and second fit of the logistic regression model on all of the MRI studies in Validation Set 1

| | Coefficient | Standard Error | Bootstrapped Mean (95% CI) |
|---|---|---|---|
| Fit 1 | | | |
| Intercept | −6.44 | 0.01 | −6.68 (−7.86, −5.84) |
| FLAIR | 1.98 | 0.00 | 2.06 (1.61, 2.45) |
| $g$FLAIR(10) | 7.73 | 0.03 | 6.62 (1.53, 11.83) |
| $g$FLAIR(20) | −6.87 | 0.06 | −4.87 (−14.47, 5.70) |
| PD | −0.46 | 0.00 | −0.50 (−0.87, −0.09) |
| $g$PD(10) | −2.18 | 0.02 | −1.91 (−5.10, 1.27) |
| $g$PD(20) | 2.00 | 0.03 | 1.69 (−3.88, 7.11) |
| T2 | 0.64 | 0.00 | 0.65 (0.38, 0.98) |
| $g$T2(10) | 0.53 | 0.02 | 0.41 (−2.80, 3.50) |
| $g$T2(20) | −0.03 | 0.04 | −0.45 (−5.16, 4.05) |
| T1 | 1.52 | 0.00 | 1.56 (1.27, 1.89) |
| $g$T1(10) | 8.68 | 0.02 | 8.84 (6.19, 11.66) |
| $g$T1(20) | −15.44 | 0.03 | −15.52 (−20.20, −10.72) |
| FLAIR * $g$FLAIR(10) | 0.10 | 0.01 | 0.50 (−1.12, 2.50) |
| FLAIR * $g$FLAIR(20) | −5.02 | 0.03 | −5.75 (−9.34, −2.53) |
| PD * $g$PD(10) | −1.76 | 0.01 | −2.01 (−3.29, −0.67) |

TABLE 1-continued

Regression coefficients from first and second fit of the logistic regression model on all of the MRI studies in Validation Set 1

| | Coefficient | Standard Error | Bootstrapped Mean (95% CI) |
|---|---|---|---|
| PD * $\mathcal{G}$PD(20) | 1.80 | 0.02 | 2.16 (0.30, 4.30) |
| T2 * $\mathcal{G}$T2(10) | −0.10 | 0.01 | −0.06 (−1.41, 1.13) |
| T2 * $\mathcal{G}$T2(20) | −1.47 | 0.02 | −1.45 (−3.29, 0.50) |
| T1 * $\mathcal{G}$T1(10) | −0.64 | 0.01 | −0.72 (−1.62, 0.25) |
| T1 * $\mathcal{G}$T1(20) | 0.41 | 0.02 | 0.46 (−1.70, 2.25) |
| Fit 2 | | | |
| Intercept | −5.66 | 0.01 | −5.98 (−7.09, −5.12) |
| FLAIR | 1.87 | 0.00 | 1.96 (1.52, 2.48) |
| $\mathcal{G}^2$FLAIR(10) | 3.96 | 0.04 | 2.82 (−2.81, 10.31) |
| $\mathcal{G}^2$FLAIR(20) | −3.19 | 0.06 | −1.44 (−15.18, 10.25) |
| PD | −0.78 | 0.00 | −0.80 (−1.21, −0.29) |
| $\mathcal{G}^2$PD(10) | −1.20 | 0.03 | −0.97 (−4.71, −0.29) |
| $\mathcal{G}^2$PD(20) | 3.16 | 0.04 | 2.83 (−2.96, 7.97) |
| T2 | 0.91 | 0.00 | 0.91 (0.56, 1.28) |
| $\mathcal{G}^2$T2(10) | −2.63 | 0.03 | −2.51 (−6.33, 1.47) |
| $\mathcal{G}^2$T2(20) | 0.10 | 0.04 | −0.37 (−8.44, 6.05) |
| T1 | 1.90 | 0.00 | 1.92 (1.49, 2.40) |
| $\mathcal{G}^2$T1(10) | 5.38 | 0.02 | 5.83 (2.61, 9.20) |
| $\mathcal{G}^2$T1(20) | −11.57 | 0.03 | −12.11 (−17.91, −6.78) |
| FLAIR * $\mathcal{G}^2$FLAIR(10) | 0.10 | 0.02 | 0.58 (−1.27, 2.40) |
| FLAIR * $\mathcal{G}$FLAIR(20) | −4.97 | 0.03 | −5.71 (−9.81, −1.98) |
| PD * $\mathcal{G}^2$PD(10) | −2.26 | 0.01 | −2.36 (−2.36, −1.00) |
| PD * $\mathcal{G}^2$PD(20) | 2.73 | 0.02 | 2.95 (0.36, 5.26) |
| T2 * $\mathcal{G}^2$T2(10) | 1.59 | 0.02 | 1.55 (0.15, 2.68) |
| T2 * $\mathcal{G}^2$T2(20) | −4.52 | 0.02 | −4.43 (−7.04, −2.37) |
| T1 * $\mathcal{G}^2$T1(10) | −0.82 | 0.01 | −0.86 (−1.70, 0.07) |
| T1 * $\mathcal{G}^2$T1(20) | 0.33 | 0.02 | 0.28 (−1.63, 2.01) |

Choosing a final threshold value after the second probability maps are made is a tradeoff between sensitivity and specificity. OASIS is flexible, and the appropriate false positive rate may be selected for a particular application. Table 2, below, shows the threshold values, sensitivity, and dice similarity coefficient for four different false positive rates for the model fit over all of the studies in Validation Set 1. OASIS detected lesions in many of the healthy subjects. Table 3, below, shows the mean volume of false positive lesions detected in the healthy and MS subjects for the four threshold values from Table 2. The volume of false positives for both the MS and healthy subjects is comparable.

TABLE 2

Binary segmentation thresholds with false positive rate, sensitivity and DSC for Validation Set 1

| False Positive Rate | Sensitivity | Threshold Value | DSC |
|---|---|---|---|
| 1% | 80% | 0.10 | 0.55 |
| 0.75% | 76% | 0.12 | 0.58 |
| 0.5% | 69% | 0.16 | 0.61 |
| 0.25% | 58% | 0.23 | 0.59 |

TABLE 3

Volume of false positive lession in healthy volunteers and MS subjects from Validation Set 1 (in cm$^3$): the actual mean lesion volume is 0 cm$^3$ for healthy volunteers and 11.2 cm$^3$ (IQR: [1.7 cm$^3$, 16.6 cm$^3$]) for MS subjects

| Threshold Value | Healthy Mean (IQR) | MS Mean (IQR) |
|---|---|---|
| 0.10 | 8.6 (4.6, 10.6) | 10.9 (7.6, 13.6) |
| 0.12 | 6.7 (3.1, 8.2) | 8.0 (5.2, 10.3) |
| 0.16 | 4.3 (1.5, 5.7) | 5.2 (3.0, 7.0) |
| 0.23 | 2.2 (.7, 2.8) | 2.5 (1.2, 3.5) |

3.2 Validation Set 2: Validation with Expert Ratings

Validation Set 2, described in detail in the Materials section, consists of 169 MRI studies of 149 subjects, 20 of whom had follow-up visits. These studies were acquired using a variety of imaging protocols. For Validation Set 2, manual segmentations of lesions were not available. Instead, expert evaluations of the segmentations were used for validation. A neuroradiologist evaluated the full set of studies and segmentations, while a neurologist and a radiologist evaluated a subset of these.

When using an ROC curve for classification, thresholds for subpopulations with different covariate values may need to be defined differently in order to keep false positive rates the same across those subpopulations. There are many covariates that are not explicitly accounted for in the model because Validation Set 1 is trained on volumes that are acquired as part of a homogeneous imaging protocol. These covariates include, but are not limited to, scanner and imaging acquisition parameters. Therefore, it is expected that the ROC threshold may need to be adjusted to maintain the same false positive rate from Validation Set 1 in Validation Set 2. When moving to Validation Set 2, 10 subjects are randomly sampled. Thresholds between 0.10 and 0.50 (by increments of 0.05) are applied to the probability maps, the segmentation examined and a threshold of 0.35 for Validation Set 2 empirically choosen. This threshold is the only tuning parameter in OASIS that must be adjusted when moving to a new data set, and this adjustment is very fast and intuitive to make. The OASIS model was not re-trained for Validation set 2. Only the probability threshold was adjusted by visual inspection of probability maps for 10 subjects. For the segmentation comparison, the neuroradiologist is presented with segmentations at the threshold value of 0.35 on all of the images in Validation Set 2 as well as at the threshold from Validation Set 1 with a false positive rate of 0.005, a threshold value of 0.16. The threshold value of 0.35 is referred to as the empirical adjusted threshold and the threshold value of 0.16 as the Validation Set 1 threshold.

In order to evaluate the performance of OASIS in the context of other lesion segmentation algorithms, the OASIS segmentations are compared to the segmentations produced by the open source software LesionTOADS (http://www.nitrc.org/projects/toads-cruise/). LesionTOADS runs with T1-weighted and FLAIR inputs and the default parameters. The smoothing parameter are adjusted from 0.2 to 0.4 because empirically this is found to improve the quality of the segmentations. It is important to note that LesionTOADS not only segments lesions, but also segments the other tissue classes of the brain. For this analysis, only used the lesion segmentations produced by LesionTOADS are used.

An image rating system is designed to evaluate the performance of the two segmentation algorithms. For each of the 169 studies, there are three segmentations: the LesionTOADS segmentation, the OASIS segmentation with the threshold from Validation Set 1, and the OASIS segmentation with the empirically adjusted threshold. 20 of the MRI studies are also randomly selected and created duplicates of these to assess rating reliability. The order in which the segmentations is randomized and they are presented to the neuroradiologist and randomly assigned a letter: A, B, or C, so as to blind the rater to the segmentation algorithm.

Figure 8:
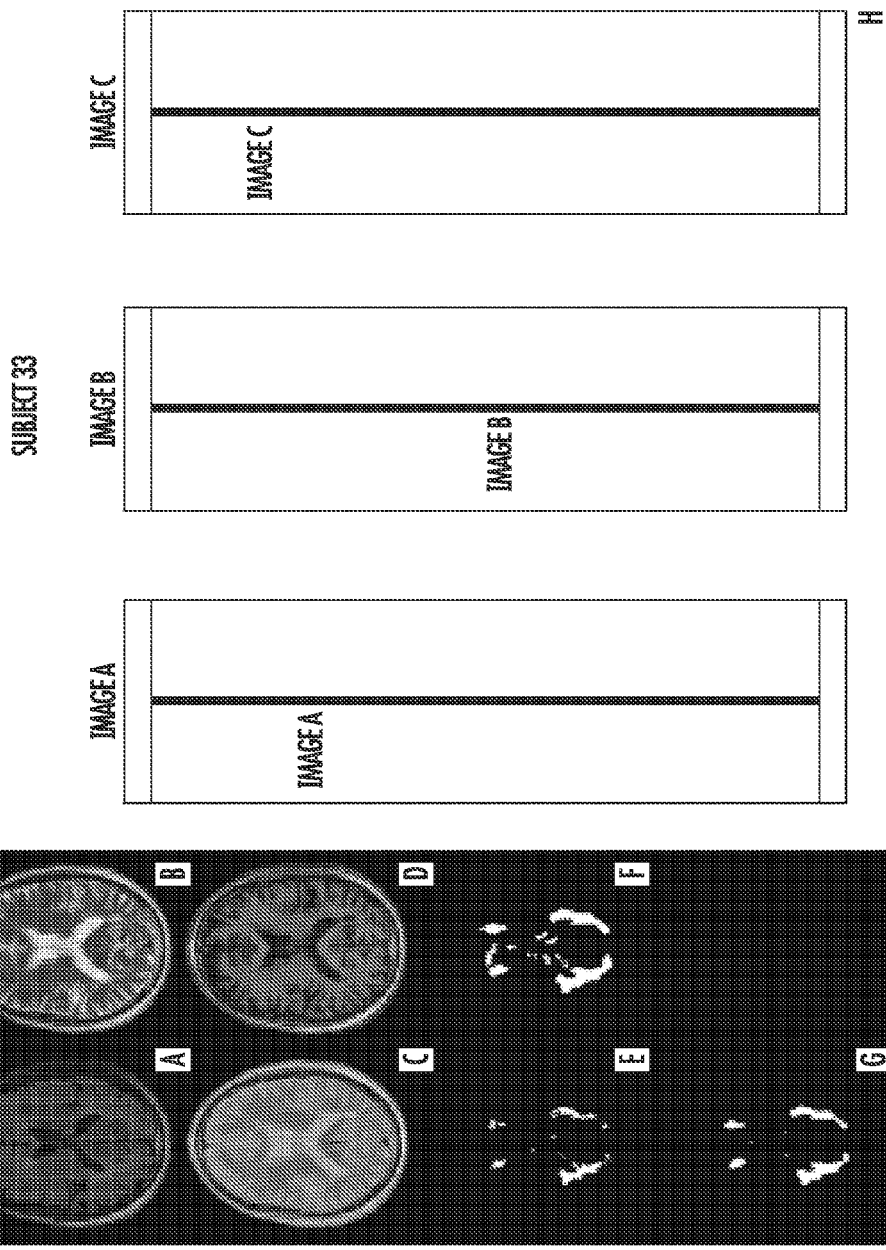
FIG. 8 shows an example of the MRI volumes, the three segmentations, and the scale for rating the segmentations, according to an embodiment of the present invention.

Each of the 189 MRI studies are presented to an experienced neuroradiologist. For each study, the neuroradiologist examines the set of three segmentations along with the original FLAIR, PD, T1-weighted, and T2-weighted volumes. The neuroradiologist then scored the performance of each of the segmentations on a continuous scale from 0 to 100, with 0 being an unusable lesion segmentation and 100 being a perfect segmentation. The neuroradiologist was presented all three segmentations simultaneously so that scores were assigned relative to one another. As manual segmentation of MS lesions on MRI is prone to great inter- and intra-observer variability, the neuroradiologist compared and rated the quality of image segmentations. FIG. 8 shows an example of the MRI volumes, the three segmentations, and the scale for rating the segmentations.

Fifty of the studies were selected to be scored with the same system by a neurologist and a radiologist in order to assess rater agreement among the three raters. The 50 studies was comprised of 45 randomly selected studies with 5 of the studies repeated to assess rater reliability.

3.3 Neuroradiologist Rating Results

Figure 9:
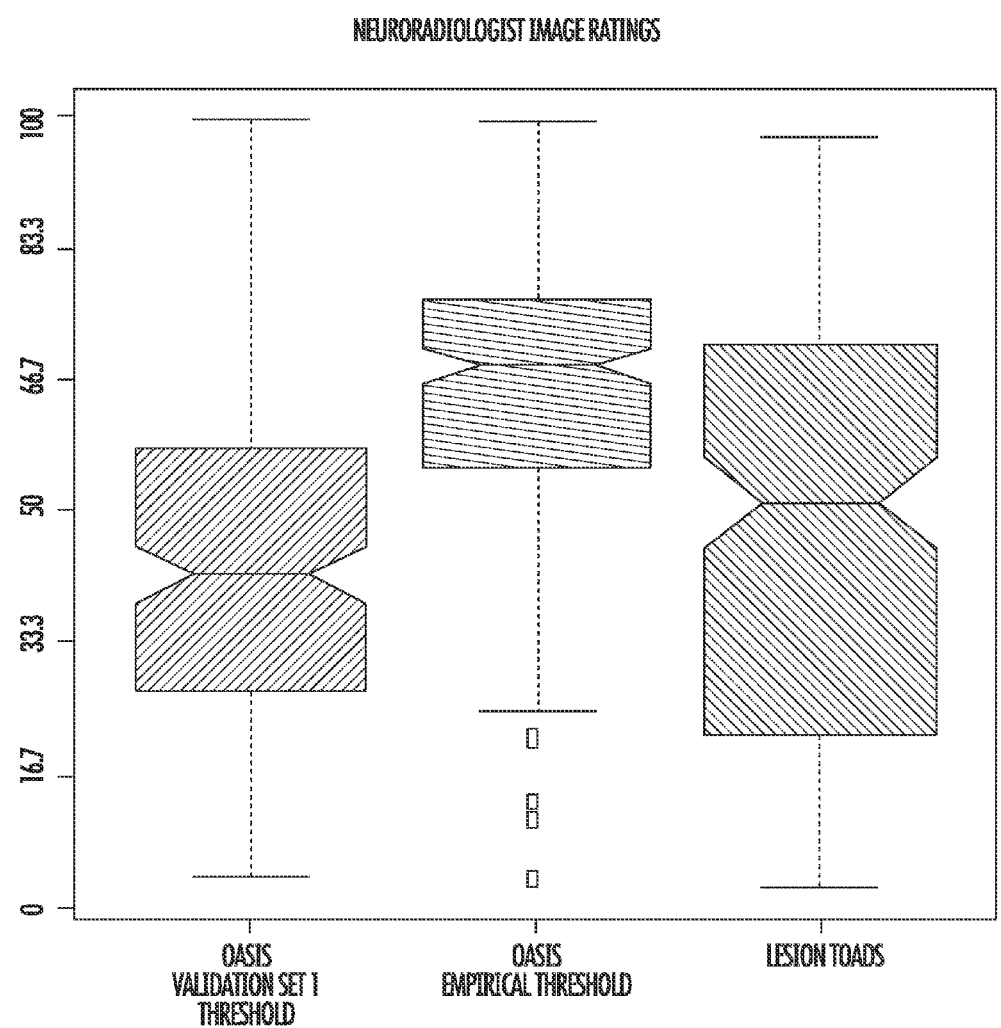
FIG. 9 shows a notched box plot of summary statistics for the scores from the neuroradiologist ratings of the three segmentations for all 189 studies according to an embodiment of the present invention.

Table 4 contains summary statistics for the scores from the neuroradiologist ratings of the three segmentations for all 189 studies. FIG. 9 shows a notched box plot of these findings. From the box plot it can be see that there is a statistically significant difference between the medians for all three groups. It also can be seen that the OASIS Validation Set 1 threshold segmentations and the LesionTOADS segmentations have a much lower first quantile than the OASIS empirical threshold segmentations.

TABLE 4

Summary statistics of image ratings of Validation Set 2 for neuroradiologist on 180 studies

|  | OASIS Validation Set 1 Threshold | OASIS Empirical Threshold | LesionTOADS |
|---|---|---|---|
| Minimum | 3.7 | 3.7 | 2.7 |
| $1^{st}$ Quantile | 27.3 | 55.7 | 21.7 |
| Median | 42.0 | 68.3 | 51.0 |
| Mean | 43.2 | 64.1 | 47.5 |
| $3^{rd}$ Quantile | 57.7 | 76.3 | 71.0 |
| Maximum | 99.3 | 99.0 | 97.3 |

Figure 10:
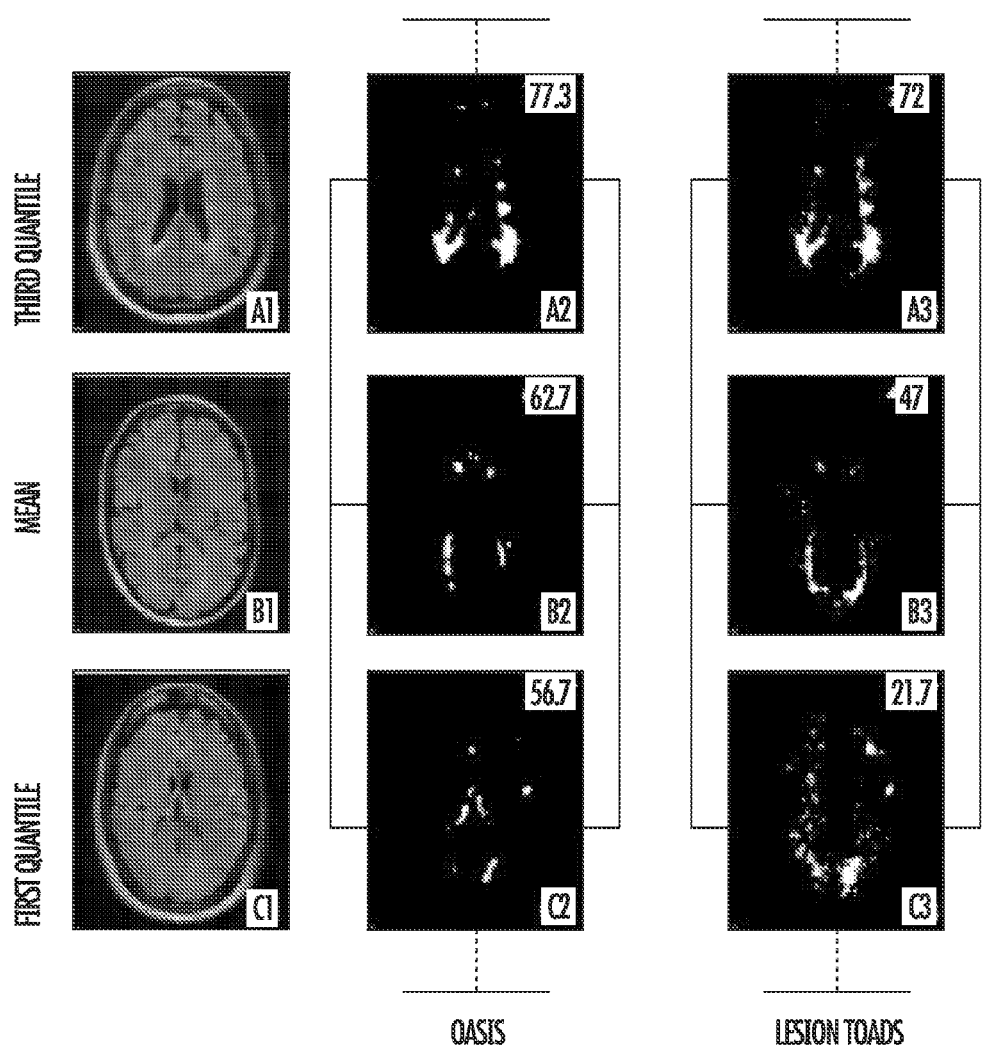
FIG. 10 shows a visual representation of the first quantile, mean, and third quantile for both the OASIS empirical threshold and the LesionTOADS segmentation, according to an embodiment of the present invention.

For this analysis, the focus is mainly on the difference between the OASIS empirical threshold and the Lesion-TOADS segmentation, as the OASIS Validation Set 1 threshold did not perform well on this new data set. This is expected, as the probability map threshold needs to be adjusted to maintain the same false positive rate when moving to a new data set. FIG. 10 shows a visual representation of the first quantile, mean, and third quantile for both the OASIS empirical threshold and the LesionTOADS segmentation. The first column shows the FLAIR volume for three subjects, the second column the OASIS empirical threshold segmentation, and the third column the Lesion-TOADS segmentation. Row A is a selected slice from a single subject with ratings for both the LesionTOADS and OASIS empirical threshold segmentations that were nearest to the third quantile of the neuroradiologist's ratings of each method. These scores are shown in the upper right hand corner of each of the segmentations. Row B is a selected slice from a subject with scores for the two segmentations that were nearest to the mean. Row C is a selected slice from a subject with scores for the two segmentations that were nearest to the first quantile. FIG. 10 reiterates that the LesionTOADS segmentations have a much lower first quantile than OASIS; LesionTOADS had a number of segmentations with very low scores.

A paired t-test is performed to assess the di_erence in the means of the OASIS empirical threshold scores and the LesionTOADS scores. This difference was found to be 16.6, which is 17% of the range of scores (0,100), with a 95% confidence interval of (13.3, 20.0), p-value $<1.0 \times 10^{-14}$.

The OASIS empirical threshold was ranked higher than LesionTOADS segmentation in 146 (95% CI: [135, 157]) of the 189 cases or 77% (95% CI: [71%, 83%]). The subjects are nonparametrically bootstrapped with replacement to produce the confidence intervals for the rankings. To assess rater reliability among the 20 duplicated MRI studies, the intraclass correlation coefficient is calculated: 0.61 (95% CI: [0.69, 0.81]). The rankings for the LesionTOADS images and the OASIS empirical threshold are preserved in the duplicate rankings for 17 of the 20 images (95% CI: [14, 20]). The intraclass correlation coefficient for each of the segmentation methods for the subjects with longitudinal follow up studies can be found in Table 5. No statistically significant difference is found for the reliability among the three segmentation methods. The subjects are nonparametrically bootstrapped with replacement to produce the confidence intervals for both the intraclass correlation coefficients and the rankings.

TABLE 5

Longitudinal reliability of segmentations for Validation Set 2, neuroradiological ratings on 20 pairs of baseline and follow up studies

|  | Intraclass Correlation Coefficient (95% CI) |
|---|---|
| OASIS, Validation Set 1 Threshold | 0.49 (0.13, 0.76) |
| OASIS, Empirical Threshold 2 | 0.60 (0.25, 0.86) |
| LesionTOADS | 0.55 (0.11, 0.81) |

The neuroradiologist was then unblinded and reviewed the three segmentations, providing comments about the strengths and weaknesses of each. The OASIS empirical threshold performed much better than the OASIS Validation Set 1 threshold. The neuroradiologist reported a preference for the smoothness of the OASIS segmentations in contrast to the LesionTOADS segmentation, which often appeared speckled. The OASIS segmentations often had artifacts in the pineal glands and the choroid plexus of the ventricles. This may be explained by the fact that OASIS was trained on FLAIR images acquired before a gadolinium-based contrast agent was administered to the patient, while the validation was done with FLAIR images that were acquired after gadolinium administration. Voxels in the choroid plexus and pineal glands, which enhance with gadolinium, were brighter and were thus misclassified as lesion. Lesion-TOADS does not make a similar error, as it imposes topological constraints that preclude these structures from being identified as lesions. Further refinements of OASIS may account for such complex changes of protocol. The LesionTOADS segmentations were more variable than those of OASIS and did not perform well on cases with low lesion load, as shown in FIG. 10. The OASIS segmentation had systematic errors in the medial frontal cortex and the brainstem. On the other hand, LesionTOADS avoided false positives in the brainstem because it only segments lesions in the cerebrum.

3.4 Rater Agreement: Neuroradiologist, Neurologist, and Radiologist

Figure 11:
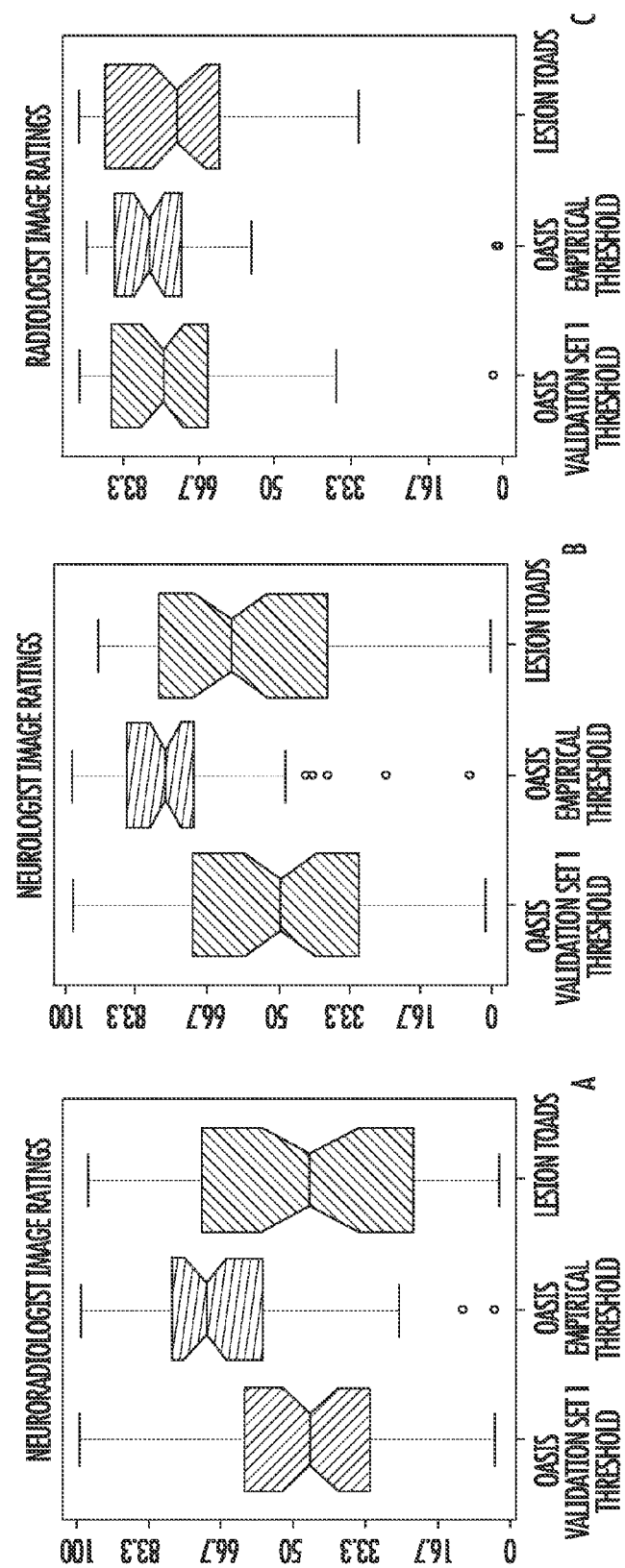
FIG. 11 shows a notched box plot for each radiologist rating of the three segmentations for the set of 50 studies selected to assess rater reliability, according to an embodiment of the present invention.

Table 6 contains summary statistics for the scores from the neuroradiologist, neurologist, and radiologist ratings of the three segmentations for the set of 50 studies selected to asses rater reliability. FIG. 11 shows a notched box plot for each rater of these findings. From the box plot it can be seen that there is a statistically significant difference between the medians for all three segmentations for the neuroradiologist and neurologist. There was not a statistically significant difference in the medians of the scores for the three segmentations by the radiologist. Moreover, all three raters indicated that the OASIS Validation Set 1 segmentations and the LesionTOADS segmentations have a much lower first quantile than the OASIS empirical threshold segmentations.

TABLE 6

Mean and standard deviation of the rating from the neuroradiologist, neurologist, and radiologist for OASIS Validation Set 1 threshold, OASIS empirical threshold and LesionTOADS on 50 studies from Validation Set 2; mean difference between OASIS empirical threshold and Lesion-TOADS and percentage of times OASIS was ranked higher than LesionTOADS on these images

| | OASIS Validation Set 1 Mean (SD) | OASIS Empirical Mean (SD) | LesionTOADS Mean (SD) | Mean Difference (95% CI) | Percentage Rank (95% CI) |
|---|---|---|---|---|---|
| Neuroradiologist | 46.3 (22.0) | 66.1 (20.2) | 47.3 (27.2) | 18.7 (11.2, 26.3) | 76% (64%, 88%) |
| Neurologist | 48.7 (24.3) | 73.1 (18.5) | 56.6 (26.0) | 16.5 (7.0, 25.9) | 66% (52%, 78%) |
| Radiologist | 71.6 (19.6) | 74.1 (17.0) | 71.8 (16.5) | 2.3 (−4.2, 8.8) | 52% (38%, 66%) |

Again, the focus is mainly on the difference between the OASIS empirical threshold and the LesionTOADS segmentation. A paired t-test is performed to assess the difference in the means of the OASIS empirical threshold scores and the LesionTOADS scores. These differences can be found in Table 6. The mean for the OASIS empirical threshold was greater than the mean for the LesionTOADS scores for all three raters. This difference was found to be statistically significant for both the neuroradiologist and neurologist, (p-values $<1.0\times10^{-4}$ and $<1.0\times10^{-3}$, respectively), but not for the radiologist, (p-value 0.5). The neuroradiologist and the neurologist tended to spread their scores more and this allowed better comparison of the segmentation algorithms. Table 6 also shows the percentage of time the OASIS empirical threshold was ranked higher than LesionTOADS segmentation in the 50 studies. The subjects nonparametrically bootstrapped with replacement to produce the confidence intervals for the rankings.

To assess rater reliability among the 5 duplicated MRI studies, the intraclass correlation coefficient are calculated and the number of times the rankings for the LesionTOADS images and the OASIS empirical threshold were preserved. These results can be found in Table 7. The subjects are nonparametrically bootstrapped with replacement to produce the confidence intervals for both the intraclass correlation coefficients and the rankings.

TABLE 7

Rater reliability of image ratings and rankings of OASIS empirical threshold versus Lesion TOADS for neuroradiologist, neurologist, and radiologist on 5 repeated studies from Validation Set 2

| | Intraclass Correlation Coefficient (95% CI) | Rank (95% CI) |
|---|---|---|
| Neuroradiologist | 0.55 (0.21, 0.82) | 4 (2.5) |
| Neurologist | 0.32 (−0.10, 0.68) | 4 (2.5) |
| Radiologist | −0.38 (−0.35, 0.71) | 2 (0.4) |

Table 8 shows the rater agreement for the ranking of the OASIS empirical threshold versus LesionTOADS. The rankings of the scores are used to assess rater agreement rather than the scores themselves, because, as shown from the intraclass correlation coefficient, the scores are not very reliable. The order in which the observers rank the segmentations, on the other hand, is quite reliable. The kappa statistic is calculated to assess the reliability of the rankings for each pair of raters and nonparametrically bootstrapped with replacement the subjects to produce the confidence intervals for the kappa statistics.

TABLE 8

Rater agreement for rankings of OASIS empirical threshold versus LesionTOADS for neuroradiologist, neurologist, and radiologist on 50 studies from Validation Set 2

| | Kappa Statistic (95% CI) |
|---|---|
| Neuroradiologist, Neurologist | 0.47 (0.20, 0.75) |
| Neuroradiologist, Radiologist | 0.02 (−0.26, 0.30) |
| Neurologist, Radiologist | −0.09 (−0.37, 0.19) |

4 Discussion

OASIS may be used to assist or even replace manual segmentation of MS lesions in the brain. After training, the fully automatic method does not require human input and avoids the variability introduced by manual segmentation. Using the explicit form of the statistical model, OASIS can easily be adapted and trained for cases where more or fewer imaging sequences are available. The potential practical utility of OASIS is high; OASIS may assist in standardizing scoring of MS lesion load in clinical trials with multiple sites and scanners. OASIS is likely to be both time- and cost-saving in large-scale studies employing neuroimaging endpoints in MS.

A key feature of OASIS is robustness to changes in imaging center and protocol. This is shown in the results from the expert ratings of the OASIS performance on Validation Set 2. MRI volumes are acquired in arbitrary units, and proper intensity normalization provides intensities with a common interpretation across studies and centers, allowing the regression coefficients to generalize to new data sets. A recalibration of the population-level segmentation threshold is necessary for each new data set but can be done on a fairly limited number of subjects, as in the example from this paper. This recalibration is also very intuitive and does not require multiple iterations of segmentations. In this work, performance on MRI data acquired at a separate imaging center is evaluated from the data the method was trained on. This is very important to avoid extrapolation biases; it cannot be assumed that an algorithm's performance on a training set or simulated data will generalize to a new data set. In particular, over-fitting any one particular data set necessarily hurts the generalizability of an algorithm.

In contrast to many automatic segmentation techniques, OASIS is computationally fast. While training the model on the 131 studies from Validation Set 1 takes five hours on a standard workstation, this process is only conducted once. The results from this are summarized as the two sets of 21 coefficients in model [1]. Also, the model may be trained on fewer studies, as shown in the partial ROC analysis within Validation Set 1; the performance of the model remains stable when trained on subsets of 20 studies. Using this fitted model to generate a probability map of the entire brain from a set of new images takes only 30 minutes. These times are for standard workstations and are expected to drop dramatically with multi-core parallel computing and improved technologies. The Gaussian smoothing is the slowest step of the algorithm, and these computations can be parallelized to substantially decrease the time of the entire algorithm to approximately 5 minutes.

Other methods of capturing inhomogeneities may be used in the OASIS model as an alternative to the BLUR volumes. Alternative smoothers may be used instead of the Gaussian kernel and may be more appropriate in other applications. The Gaussian filter is used because it is widely used, can be applied to any image, and is relatively computationally fast. The OASIS modeling framework is very flexible, however, and can be adapted for other methods of capturing the bias field and regional intensity variation.

Lesions that are hypointense on FLAIR, because of high free water content, are not detected by OASIS. The method models only candidate voxels, the top 15 percent of voxels in the cerebral matter-masked FLAIR volume, to minimize the number of false positives. In the FLAIR volume, such lesions are characterized by hypointensities in the center of a lesion and hyperintensities around the edges. Therefore the center of the lesions is excluded from the candidate voxels. Like other voxel-based methods, OASIS is sensitive to major misregistrations within an MRI study. However, OASIS is robust to minor errors in registration. By simultaneously comparing data from multiple sequences and only considering candidate voxels, OASIS is able to distinguish between artifacts and lesion.

OASIS is not an atlas-based method and therefore does not take into account anatomical information during segmentation, such as tissue class. Further incorporation of anatomical information, such as the tissue class segmentations from LesionTOADS, may help to avoid lesions false positives in areas where there is prior knowledge that lesion presence is low and where OASIS made systematic false positives, such as the medial frontal cortex and the brainstem. Also, this could be used to help with the false positives in the pineal glands and the choroid plexus of the ventricles in the post-contrast FLAIR as these are areas where lesions do not occur in MS.

OASIS uses a voxel-level model for assessing the outcome. The assumption of independence between voxels is imperfect, as lesions consist of clusters of voxels. In this work smoothing is used in the BLUR volumes and smoothing of the predicted probabilities of the model is used to incorporate the spatial nature of the data. Nevertheless, further incorporation of neighboring voxel information is warranted.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A method of analysis of multi-sequence MRI data for neurological disorders comprising:
obtaining intensity information using an MRI modality;
assigning a probability of a presence of a neurological abnormality using a logistic regression model;
producing results in the form of regression coefficients that can be applied to the multi-sequence MRI data;
adjusting for intensity inhomogeneities;
sequentially blurring images comprising the multi-sequence MRI data using Gaussian blurs with varying kernel sizes resulting in blurred images;
oversmoothing the images;
maintaining regional features of the multi-sequence MRI data, as well as spatial inhomogeneities;
removing local voxel-specific features;
providing a multi-scale procedure, thereby allowing for different resolutions in terms of the regional features of interest wherein the neurological abnormalities are included in the blurred images;
isolating probable abnormalities from each modality, each of the blurred images;
including in a logistic regression model having estimates of voxel-specific probability of the voxel being part of the abnormality in an interaction between the images and the blurred images;
removing said abnormality from the image;
reblurring said image resulting in a reblurred image;
providing a refined description of regional patterns including spatial inhomogeneity and inhomogenieity and underlying anatomy of said abnormalities;
providing a segmentation for identifying the neurological abnormality in a subject; and
locating a position of the neurological abnormality in the subject.

2. The method of claim 1 wherein said multi-sequence MRI data comprises T1-weighted, T2-weighted, T2-weighted fluid attenuation inversion recovery (FLAIR), and PD-weighted images.

3. The method of claim 1 further comprising pre-processing said multi-sequence MRI data using standard image analysis tools.

4. The method of claim 1 further comprising normalizing the multi-sequence MRI data using a normalization procedure.

5. The method of claim 1 further comprising:
using the reblurred images and said normalized data and the interactions between the images and the blurred images;

refitting logistic regression model;
refining estimates of said voxel-specific probability of said abnormality;
directly interpreting said probabilities; and
yielding binary segmentation maps.

6. The method of claim 5 wherein said abnormality is a brain lesion and further comprising utilizing a single cross-sectional imaging study and identifying how much said lesion load said subject has and where in the brain said lesions exist.

7. The method of claim 6 wherein said abnormality is associated with multiple sclerosis.

8. The method of claim 1 further comprising:
resampling said multi-sequence MRI data over time;
reestimating coefficients and performance using partial ROC methods; and
obtaining a robust analysis of the image data.

9. A system for analysis of multi-sequence MRI data for neurological disorders comprising:
an MRI imaging system configured to collect and transmit multi-sequence MRI data as well as images related to the neurological disorder;
a data storage device configured to store the multi-sequence MRI data and images related to the neurological disorder;
a computing device configured for:
processing the multi-sequence MRI data and images;
providing a segmentation for identifying a neurological abnormality in a subject and locate a position of said abnormality in said subject;
isolating probable abnormalities from each modality, each of the blurred images;
including in a logistic regression model having estimates of voxel-specific probability of the voxel being part of the abnormality in an interaction between the images and the blurred images;
removing said abnormality from the image;
reblurring said image resulting in a reblurred image;
providing a refined description of regional patterns including spatial inhomogeneity and inhomogenieity and underlying anatomy of said abnormalities;
using the reblurred images and said normalized data and the interactions between the images and the blurred images;
refitting logistic regression model;
refining estimates of said voxel-specific probability of said abnormality;
directly interpreting said probabilities; and
yielding binary segmentation maps.

10. The system of claim 9 wherein said multi-sequence MRI data comprises T1-weighted, T2-weighted, T2-weighted fluid attenuation inversion recovery (FLAIR), and PD-weighted images.

11. The system of claim 9 wherein the computing device is further configured to pre-process said multi-sequence MRI data using standard image analysis tools.

12. The system of claim 9 wherein the computing device is further configured to normalize the multi-sequence MRI data using a normalization procedure.

13. The system of claim 9 wherein the computing device is further configured to sequentially blur images comprising the multi-sequence MRI data using Gaussian blurs with varying kernel sizes resulting in blurred images.

14. The system of claim 13 wherein the computing device is further configured to: oversmooth the images;
maintain regional features of the multi-sequence MRI data, as well as spatial inhomogeneities; and
remove local voxel-specific features.

15. The system of claim 14 wherein the computing device is further configured to provide a multi-scale procedure, thereby allowing for different resolutions in terms of the regional features of interest wherein the neurological abnormalities are included in the blurred images.

16. The system of claim 9 wherein said abnormality is a brain lesion and further comprising the computing device being configured to utilize a single cross-sectional imaging study and identify how much said lesion load said subject has and where in the brain said lesions exist.

17. The system of claim 9 wherein the abnormality is associated with multiple sclerosis.

18. The system of claim 9 wherein the computing device is further configured to
resample said multi-sequence MRI data over time;
reestimate coefficients and performance using partial ROC methods; and
obtain a robust analysis of the image data.

19. A method of analysis of multi-sequence MRI data for neurological disorders comprising:
creating a brain tissue mask using multi-sequence MRI data;
normalizing MRI volumes for intensity;
constructing initial BLUR volumes using the brain tissue mask and the normalized MRI volumes;
fitting an initial logistical regression model to the BLUR volumes;
performing lesion segmentation of any neurological abnormalities;
reblurring the BLUR volumes resulting in reblurred images;
providing a refined description of regional patterns including spatial inhomogeneity and inhomogenieity and underlying anatomy of said abnormalities;
using the reblurred images and said normalized data and the interactions between the images and the BLUR volumes;
refitting logistic regression model;
refining estimates of said voxel-specific probability of said abnormality;
constructing a final BLUR volume with any neurological abnormalities removed;
fitting a final logistical regression model to the final BLUR volume; and
creating a probability map and neurologic abnormality lesion segmentation.

* * * * *